United States Patent
Zhan

(10) Patent No.: US 12,071,408 B2
(45) Date of Patent: *Aug. 27, 2024

(54) MULTI-TARGETED TYROSINE KINASE INHIBITORS EFFECTIVE IN ANTITUMOR USES

(71) Applicant: Shanghai AB PharmaTech Ltd., Shanghai (CN)

(72) Inventor: Zheng-Yun James Zhan, Shanghai (CN)

(73) Assignee: Shanghai AB PharmaTech Ltd., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/819,157

(22) Filed: Aug. 11, 2022

(65) Prior Publication Data

US 2023/0123696 A1 Apr. 20, 2023

(30) Foreign Application Priority Data

Aug. 12, 2021 (CN) .......................... 202110924393.5

(51) Int. Cl.
| | |
|---|---|
| *C07D 215/233* | (2006.01) |
| *A61K 31/44* | (2006.01) |
| *A61K 31/47* | (2006.01) |
| *A61K 31/4709* | (2006.01) |
| *A61K 31/496* | (2006.01) |
| *A61K 31/506* | (2006.01) |
| *A61K 31/513* | (2006.01) |
| *A61K 45/06* | (2006.01) |
| *A61P 11/00* | (2006.01) |
| *A61P 35/00* | (2006.01) |
| *A61P 35/02* | (2006.01) |
| *C07D 215/48* | (2006.01) |
| *C07D 401/06* | (2006.01) |
| *C07D 401/12* | (2006.01) |
| *C07D 405/12* | (2006.01) |

(52) U.S. Cl.
CPC ......... *C07D 215/233* (2013.01); *A61K 31/44* (2013.01); *A61K 31/47* (2013.01); *A61K 31/4709* (2013.01); *A61K 31/496* (2013.01); *A61K 31/506* (2013.01); *A61K 31/513* (2013.01); *A61K 45/06* (2013.01); *A61P 11/00* (2018.01); *A61P 35/00* (2018.01); *A61P 35/02* (2018.01); *C07D 215/48* (2013.01); *C07D 401/06* (2013.01); *C07D 401/12* (2013.01); *C07D 405/12* (2013.01); *C07B 2200/05* (2013.01)

(58) Field of Classification Search
None
See application file for complete search history.

(56) References Cited

U.S. PATENT DOCUMENTS

| | | | |
|---|---|---|---|
| 7,994,159 B2 * | 8/2011 | Yamamoto | A61P 43/00 514/183 |
| 2019/0375714 A1 | 12/2019 | Si et al. | |
| 2020/0262791 A1 * | 8/2020 | Zhang | A61P 35/00 |

FOREIGN PATENT DOCUMENTS

CN 113480479 A 10/2021

OTHER PUBLICATIONS

Novel method for the synthesis of lenvatinib using 4-nitrophenyl cyclopropylcarbamate and their pharmaceutical salts Sadineni et al. Chemical Papers (2021) 75:1475-1483 Published online: Nov. 3, 2020 (Year: 2020).*
International Search Report issued Oct. 24, 2022 in International Application No. PCT/CN2022/112014.
International Search Report issued Oct. 24, 2022 in International Application No. PCT/CN2022/112011.

* cited by examiner

*Primary Examiner* — Jeffrey S Lundgren
*Assistant Examiner* — Eric Tran
(74) *Attorney, Agent, or Firm* — Sughrue Mion, PLLC

(57) ABSTRACT

Disclosed are compounds of Formula III, their stereoisomers, tautomers, deuterates, pharmacologically acceptable salts, or hydrates thereof, methods of their preparation and pharmaceutical compositions comprising such compounds. The Formula III compounds are useful and highly effective as multi-targeted tyrosine kinase inhibitors in treating several kinds of cancers such as liver cancer, bladder cancer, thyroid cancer, cervical cancer, leukemia.

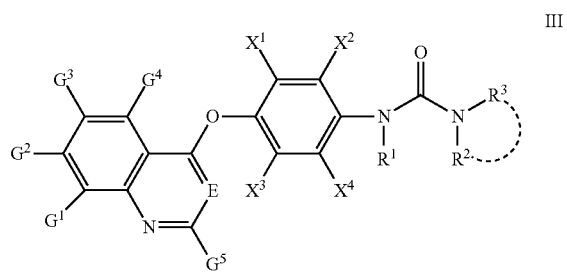

10 Claims, No Drawings

MULTI-TARGETED TYROSINE KINASE INHIBITORS EFFECTIVE IN ANTITUMOR USES

CROSS-REFERENCE TO RELATED APPLICATIONS

The present application claims priority to Chinese patent application No. CN202110924393.5, filed on Aug. 12, 2021, the contents of which are incorporated herein by reference.

FIELD OF THE INVENTION

The present invention relates to a novel class of antitumor compounds, and their uses as multi-targeted tyrosine kinase inhibitors (TKI) in treating different kinds of cancers such as liver cancer, bladder cancer, thyroid cancer, cervical cancer, and leukemia.

BACKGROUND OF THE INVENTION

Protein tyrosine kinases (PTKs) are the largest known protein superfamily, and they are important hubs for extracellular signaling into the cell. The protein tyrosine kinases play an important role in the regulation of cell proliferation and differentiation. Abnormal expression of PTKs activates a series of downstream signaling pathways, causing a cascade response, resulting in disruption of cell proliferation regulation and ultimately leading to tumor formation. Tyrosine kinases can be divided into receptor-type tyrosine kinases (RTK) and non-receptor-type tyrosine kinases (nRTK). RTKs include Vascular Endothelial Growth Factor Receptor (VEGFR), Fibroblast Growth Factor Receptor (FGFR), Epidermal Growth Factor Receptor [abb. as EGFR, HER1, or ErbB-1, is a member of the epidermal growth factor receptor (HER) family], tyrosine kinase membrane receptor (c-Met), platelet-derived growth factor receptor α (PDGFRα), and RET (RE arranged during Transfection, a transmembrane receptor tyrosine kinase) etc., these RTKs are closely associated with oncological diseases and their targeted therapies.

So far, more than 80% of kinases have been used as targets for therapeutic drug development. It has been reported that pathological increases in vascular endothelial formation are associated with the pathogenesis or progression of various diseases, and that the proliferation of solid tumors is dependent on angiogenesis. Therefore, drugs that effectively inhibit the tyrosine kinases VEGFR1-3, FGFR1-4, EGFR, C-MET, RET, PDGFRα and other tyrosine kinase (RTK) targets mentioned above have become the main targeted therapies for refractory solid tumors. For example, FGFR4 is highly expressed in cancers such as liver cancer, bladder cancer, renal cancer, thyroid, gastric cancer, colon cancer and esophageal cancers.

Currently, most of the molecularly targeted antitumor drugs marketed are protein tyrosine kinase inhibitors (PTKI) targeting PTK, for example, the small molecule urea compounds that have better inhibitory effect on tyrosine kinase VEGFR1-3 and are clinically used for the treatment of hepatocellular carcinoma include Sorafenib, Regorafenib, and Lenvatinib (which has better inhibitory effect on both tyrosine kinase VEGFR1-3 and FGFR1-4) (Ref-1), which has a better antitumor effect in clinical treatment.

The purpose of the present invention is to develop a novel multi-targeted tyrosine kinase inhibitor (TKI) with higher tyrosine kinase inhibiting activity and lower toxicity and side effects through the innovative design of small molecule structures and their functional groups, which can be more effective used for the treatment of various tumors such as liver cancer, bladder cancer, renal cancer, thyroid cancer, gastric cancer, colon cancer, esophageal cancer, lung cancer, uterine cancer, skin cancer and other related cancer diseases.

The present invention relates to a class of formula III multi-substituted anilino-urea compounds as multi-target tyrosine kinase inhibitors (TKI), with novel multi-substituted aniline building block as the focus of innovation. These compounds efficiently inhibit not only vascular endothelial growth factor receptors (VEGFR1, VEGFR2, VEGFR3) and fibroblast growth factor receptors (FGFR1-4), but also multiple important receptor tyrosine kinases (RTK) that may contribute to angiogenesis and tumor growth pathogenesis in addition to their normal cellular functions. For example, including but not limited to C-MET, RET, PDGFRα and other tyrosine kinases, which can produce relatively strong inhibition of angiogenesis and have better applications in more effective prevention and treatment of various tumors with abnormal proliferation of angiogenesis and other diseases.

The structure of urea compounds containing multi-substituted aniline groups disclosed in the present invention is based on the structural characteristics of tyrosine kinase targets, and structural modification innovation and optimization by introducing more substituents in aniline, thus developing a multi-target tyrosine kinase inhibitor (TKI) with better inhibition effect, which can treat many types of tumors more effectively.

SUMMARY OF THE INVENTION

The present invention relates to a class of novel antitumor compounds of the following formulas III with the urea based structure formed with both multi-substituted aryl-amines and alkyl-amines groups, which has been evaluated to be highly potent and effective for inhibiting more than ten kinds of tyrosine kinases such as VEGFR1-3, FGFR1-4, C-MET, RET, PDGFRα, etc. The experimental results show better inhibitory effect, better application prospect, and better safety. This invention further relates to pharmaceutical compositions comprising one or more of newly developed compounds (in a pure form or mixture of stereo-isomers, solvates, hydrates, tautomers, prodrugs, or pharmaceutically acceptable salts thereof) and another agent(s) developed as therapeutic drugs for cancer treatment.

In the first aspect, the present invention provides a compound represented by the formula III, or a stereoisomer, tautomer, deuterates, or pharmacologically acceptable salts, or hydrate thereof:

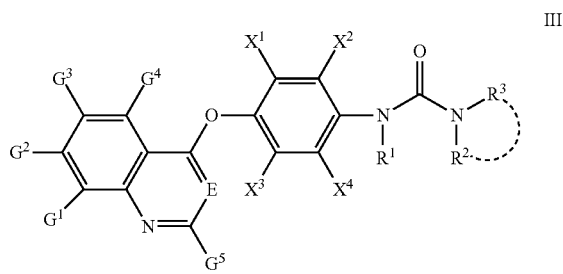

wherein:
E is independently selected from the group consisting of nitrogen (N), or CH group;

$G^1$ is independently selected from H, deuterium (D), $C_{1-20}$ alkyl group, or $C_{1-20}$ alkoxy group;

$G^2$ is independently selected from $C_{1-20}$ alkoxy, or optionally deuterium-substituted $C_{1-20}$ alkoxy group;

$G^3$ is independently selected from $-C(O)NH_2$, $-C(O)ND_2$, or an optionally substituted $C_{1-20}$ alkoxy group;

$G^4$ and $G^5$ are each, independently, selected from hydrogen (H), deuterium (D), halogen, $-CN$, $C_{1-20}$ alkyl, or $C_{1-20}$ alkoxy group;

$R^1$ is independently selected from hydrogen (H), deuterium (D), $C_{1-20}$ alkyl, $C_{3-20}$ cycloalkyl, or $C_{3-20}$ deuterated cycloalkyl group;

$R^2$ and $R^3$ are each, independently, selected from hydrogen (H), deuterium (D), $C_{1-20}$ alkyl, $C_{3-20}$ cycloalkyl, $C_{3-20}$ deuterated cycloalkyl group, or $C_{3-20}$ heterocycloalkyl group; wherein $R^2$ and $R^3$ may be linked to each other to form $C_{3-20}$ heterocyclic group with 1-3 heteroatoms.

$X^1$, $X^2$ and $X^3$ are each, independently, selected from hydrogen (H), deuterium (D), halogen, $-CN$, $-NH_2$, $C_{1-20}$ alkoxy group, or $C_{1-20}$ alkyl amino group;

$X^4$ is independently selected from H, deuterium (D), halogen, $-NH_2$, $C_{1-20}$ alkoxy, or $C_{1-20}$ alkyl amino group.

In another preferred embodiment of the invention, wherein

E is CH group,
$G^1$ is hydrogen (H);
$G^2$ is $-OCH_3$;
$G^3$ is $-C(O)NH_2$;
$G^4$ is hydrogen (H);
$G^5$ is hydrogen (H);
$R^1$ is hydrogen (H);
$R^2$ is hydrogen (H);
$R^3$ is each independently selected from $C_{3-6}$ cycloalkyl group;
$X^1$, $X^2$ and $X^3$ are each, independently, selected from halogen, $C_{1-6}$ alkoxy group, or $C_{1-6}$ alkyl amino group;
$X^4$ is independently selected from hydrogen (H), halogen, $C_{1-6}$ alkoxy group, or $C_{1-6}$ alkyl amino group.

In the second aspect, the present invention provides a method of preparing the formula III compounds.

In the third aspect, the present invention provides a method of preparing two intermediate compounds RM1 and RM1b.

In the fourth aspect, the present invention provides a method of preparing the new multi-substituted functional compound SM2-01.

In the fifth aspect, the present invention provides a pharmaceutical composition comprising one or more compounds selected from the structure III.

The sixth aspect of the present invention provides a pharmaceutical composition comprising at least one compound according to claim 1 and at least one compound selected from the group consisting of a tyrosine kinase (RTK) inhibitor.

The seventh aspect of the present invention provides a method of treating several kinds of cancers effectively with the formula III compounds, wherein the treated cancers are selected from liver cancer, bladder cancer, thyroid cancer, cervical cancer, and blood cancer.

The eighth aspect of the present invention provides a method for treating several kinds of cancers effectively by using one or more compounds of the structure III and in combination with any or combined one or more of (1) an immunomodulator, (2) PD-1 inhibitor; (3) PD-L1 inhibitor; or (4) another active ingredient that does not fall under (1)-(3) above.

Overall, all prepared new formula III compounds have been evaluated for their potency and toxicity. The present invention explores the relationship between the structures of new multi-substituted functional aryl amino group incorporated in the formula III compounds and potency of RTK inhibition, and finally to provide valuable clue and potential effective and safe antitumor RTK inhibitors.

The present invention not only relates to design and synthesize the novel antitumor formula III compounds, but also explores the relation between different novel multi-substituted functional aryl amino compounds (SM2-01~SM-22) and their activity of RTK inhibition, and finally to optimize the inhibitor structure and develop one of the best urea-based multi-targeted tyrosine kinase inhibitors.

DETAILED DESCRIPTION OF THE INVENTION

Details of the present invention are set forth in the following description for preparation and biological activity study of new RTK inhibitors III. The advantages of the present invention will be significantly observed from the following detailed description.

As used herein, the term "alkyl" refers to any linear or branched chain alkyl group having a number of carbon atoms and/or "alkylene" in the specified range, wherein one or more hydrogens could be replaced by one or more halogens.

The term "alkoxy" refers to an "alkyl-O—" group.

The term "cycloalkyl" refers to any cyclic ring of an alkane or alkene having a number of carbon atoms and/or "alkylene" in the specified range, wherein one or more hydrogens could be replaced by one or more halogens.

The term "cycloalkyl-oxy" refers to a "cycloalkyl-O—".

The term "cycloalkyl-amino" refers to a "cycloalkyl-N(Ra)—", wherein Ra is alkyl or alkylcarbonyl group.

The term "halogen" (or "halo") refers to fluorine, chlorine, bromine and iodine atoms (or referred as fluoro, chloro, bromo, and iodo).

The term "carbonyl" refers to a "—C(O)—" group.

The term "alkylcarbonyl" refers to an "alkyl-C(O)—" group.

The term "alkoxy carbonyl" refers to an "alkyl-O—C(O)—" group.

The term "alkylamino carbonyl" refers to an "alkyl-NH—C(O)—" or "dialkyl-N—C(O)—" group.

The term "sulfonamido" refers to a "—S(O)$_2$NH—" or "—S(O)$_2$N(Ra)—" group, wherein Ra is alkyl or alkylcarbonyl group.

The term "alkyl sulfonamido" refers to an "alkyl-S(O)$_2$NH—" or "alkyl-S(O)$_2$N(Ra)—" group, wherein Ra is alkyl or alkylcarbonyl group.

The term "alkoxy sulfonamido" refers to an "alkyl-O—S(O)$_2$NH—" or "alkyl-O—S(O)$_2$N(Ra)—" group, wherein Ra is alkyl or alkylcarbonyl group.

The term "heteroaryl" refers to an aryl group with 1-3 hetero atoms including 0, N, and/or S atoms.

The term "fused heteroaryl" refers to a bi-cyclic, tri-cyclic or tetra-cyclic heteroaryl group with 1-5 hetero atoms such as O, N, and/or S atoms.

The term "poly-heteroaryl" refers to a bi-, tri- or tetra-heteroaryl functional group with 1-5 hetero atoms (e.g., O, N, S, and P) in one or more fused rings.

The term "poly-heterocyclic" refers to a bi-cyclic, tri-cyclic or tetra-cyclic functional group with 1-5 hetero atoms (e.g., O, N, S, and P) in one or more fused rings.

The term "composition" is intended to encompass a product comprising the specified ingredients, as well as any product which results, directly or indirectly, from combining the specified ingredients.

The term "pharmaceutically acceptable" means that the ingredients of the pharmaceutical composition must be compatible with each other and not deleterious to the recipient thereof.

The term "effective amount" means that amount of active compound or pharmaceutical agent that elicits the biological or medicinal response in a tissue, system, animal or human that is being sought by a researcher, veterinarian, medical doctor or other clinician. The term also includes herein the amount of active compound sufficient to inhibit RTK for treating several kinds of cancers and thereby elicit the response being sought (i.e., an "inhibition effective amount"). When the active compound (i.e., active ingredient) is administered as the salt, references to the amount of active ingredient are to the free acid or free base form of the compound.

The present invention provides a class of novel antitumor RTK inhibitor compounds III, and pharmaceutically acceptable salts, and/or hydrates as RTK inhibitors with high potency. Moreover, toxicity study for MTD is determined to be 300 mg/kg for III-01.

The present invention also provides pharmaceutically acceptable salt forms of compounds of Formula III. The scope of the present invention covers acid addition salts, which are formed by bringing a pharmaceutically suitable acid into contact with a compound of the present invention.

"Pharmaceutically acceptable acid complex salts" means those salts that retain biological validity and free base properties, are not undesirable biologically or otherwise, and are formed using inorganic acids, such as, but not limited to, hydrochloric acid, hydrobromic acid, sulfuric acid, phosphoric acid, nitric acid, carbonic acid, etc.; and organic acids, such as, but not limited to: Acetic acid, benzoic acid, methanesulfonic acid, toluenesulfonic acid, or valeric acid, etc.

Synthesis of New Antitumor Compounds with General Structure III

Some of reagents and raw materials used in the present invention are commercially available, but some of reagents and raw materials were not commercially available, e.g., new SM2-01 compound was finally designed and prepared by ourselves at AB PharmaTech Lab.

Abbreviations of chemical materials, reagents, and solvents related to the synthesis of antiviral compounds in the present invention are listed in the parts of examples.

The compounds in the present invention could be synthesized by normal raw materials through several synthetic methods after designing the structure of different compounds in the present invention.

The present disclosure relates to the following key innovations:

1) The present invention optimizes the RTK inhibition activity of the formula III compounds, and one of formula III compounds, III-01, is highly potent to inhibit several important RTK targets (e.g., VEGFR1, VEGFR2, VEGFR3, FGFR1, FGFR2, FGFR3, FGFR4, and RET, EGFR, C-KET, PDGFRα, etc.).

2) The formula III compound "III-01" of the present invention has much better inhibitory effects on a variety of tumor cell lines [e.g., Hep3B 2.1-7 (hepatocellular carcinoma), RT112/84 (bladder cancer), T.T (thyroid), Hela (cervical cancer), K562 (leukemia), etc.] and can be used as targeted drugs effectively to treat several kinds of tumors or related cancers arising from RTK kinase mediated and has much better RTK targeting selectivity and safety.

3) The formula III compound "III-01" of the present invention has much better safety profile, for example: compound III-01 has not only an MTD toxicity dose of >300 mg/kg in rats, but also has the parameter of potassium channel safety hERG >30 uM (for Lenvatinib antitumor drug, its MTD is 40 mg/kg in rats, and its hERG=11.9 uM).

The present invention also provides the following two synthetic methods of the formula III compounds, and two synthetic methods have been optimized for scale-up and GMP production used for clinical trials.

Synthetic Method 1:

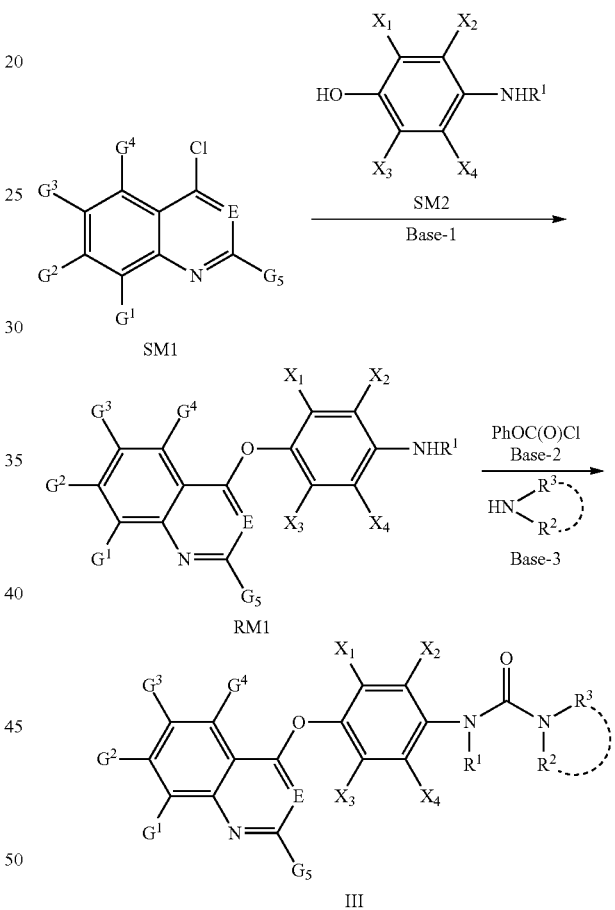

In the above method 1: the definition of E, $G^1$, $G^2$, $G^3$, $G^4$, $G^5$, $R^1$, $R^2$, $R^3$, $X^1$, $X^2$, $X^3$, $X^4$ is the same as the E, $G^1$, $G^2$, $G^3$, $G^4$, $G^5$, $R^1$, $R^2$, $R^3$, $X^1$, $X^2$, $X^3$, $X^4$ in claims 1-5, wherein, Base-1 is potassium tert-butoxide, Sol-1 is DMSO, Base-2 is pyridine, Sol-2 is DMF, Base-3 is cyclopropylamine, Sol-3 is MeCN.

The synthetic method 1 for each reaction step is as follows:

1.1 Synthesis of Intermediate RM1

In the round bottom flask, charge raw materials SM1 (1.0 eq), SM2 (1.0~1.5 eq), and potassium tert-butoxide (tBuOK, 1.2~1.5 eq) to DMSO (6~10×) respectively. Heat to 80~100°

C. under nitrogen and react, HPLC tracking detection until reach the endpoint. Slowly poured the reaction mixture into 100× ice-water with stirring, the solid will be precipitated, filtered, and washed the solid with water, dried, and the solid product RM1 was obtained.

1.2 Synthesis of Formula III Products

The above obtained RM1 and pyridine (3~5 eq) were charged to DMF (5~8×) solvent in a round bottom flask, and phenyl chloroformate (2.0~3.5 eq) was added dropwise at a temperature lower than 10° C. The reaction was carried out at room temperature after the dropwise addition was completed. HPLC tracking detection until reach the endpoint. The reaction mixture was slowly dropped into ice water (3-5×) and a solid was precipitated. The intermediate RM2 was obtained by filtration, purification, concentration, drying and other routine operations. Then the obtained intermediate RM2 and reagents SM3 (3 eq) and pyridine (3 eq) were dissolved in MeCN (10~20×) and reacted at 60° C. When the HPLC showed the endpoint, the reaction solution was slowly dropped into to 10-20× ice-water with stirring, so that the solid product was precipitated in ice water, and then the target formula III product was obtained by filtration, purification, concentration, drying and other conventional operations.

The following process is an example for preparation of the formula III compound III-01:

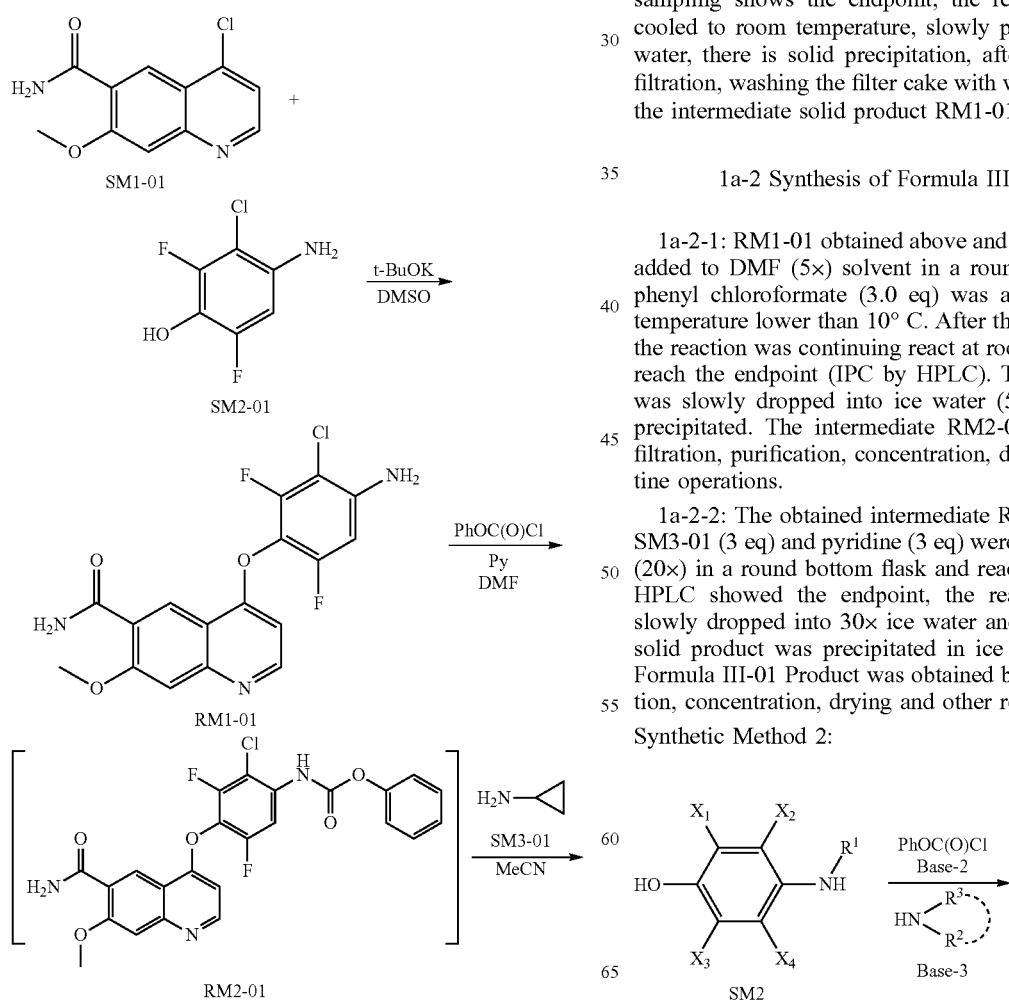

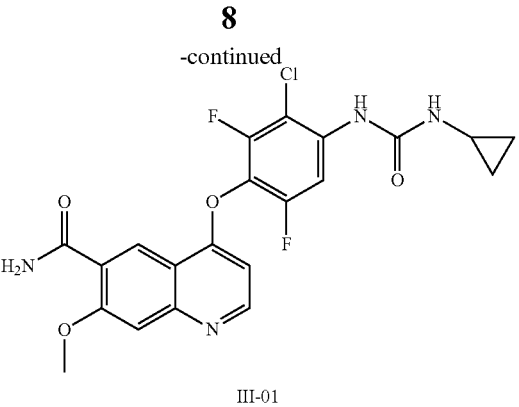

Synthetic Method 1a: Synthesis of the Formula III Compound III-01

1a-1 Synthesis of Intermediate RM1-01

To the three-necked round bottom flask, charge raw materials SM1-01 (1.0 eq), SM2-01 (1.5 eq) and potassium tert-butoxide (1.3 eq) into DMSO (10×), the reaction was react at 85° C. under nitrogen protection. After the HPLC sampling shows the endpoint, the reaction solution was cooled to room temperature, slowly poured into 100× ice water, there is solid precipitation, after thorough stirring, filtration, washing the filter cake with water, dry, and afford the intermediate solid product RM1-01.

1a-2 Synthesis of Formula III-01 Product 1a-2-1: RM1-01 obtained above and pyridine (4 eq) were added to DMF (5×) solvent in a round bottom flask, and phenyl chloroformate (3.0 eq) was added dropwise at a temperature lower than 10° C. After the dropwise addition, the reaction was continuing react at room temperature until reach the endpoint (IPC by HPLC). The reaction mixture was slowly dropped into ice water (5×) and a solid was precipitated. The intermediate RM2-01 was obtained by filtration, purification, concentration, drying and other routine operations.

1a-2-2: The obtained intermediate RM2-01 and reagents SM3-01 (3 eq) and pyridine (3 eq) were dissolved in MeCN (20×) in a round bottom flask and reacted at 60° C. When HPLC showed the endpoint, the reaction solution was slowly dropped into 30× ice water and stirred, so that the solid product was precipitated in ice water, and then the Formula III-01 Product was obtained by filtration, purification, concentration, drying and other routine operations.

Synthetic Method 2:

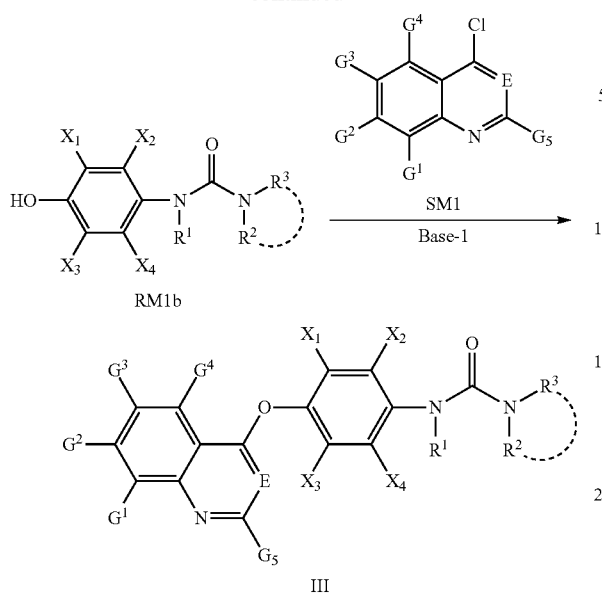

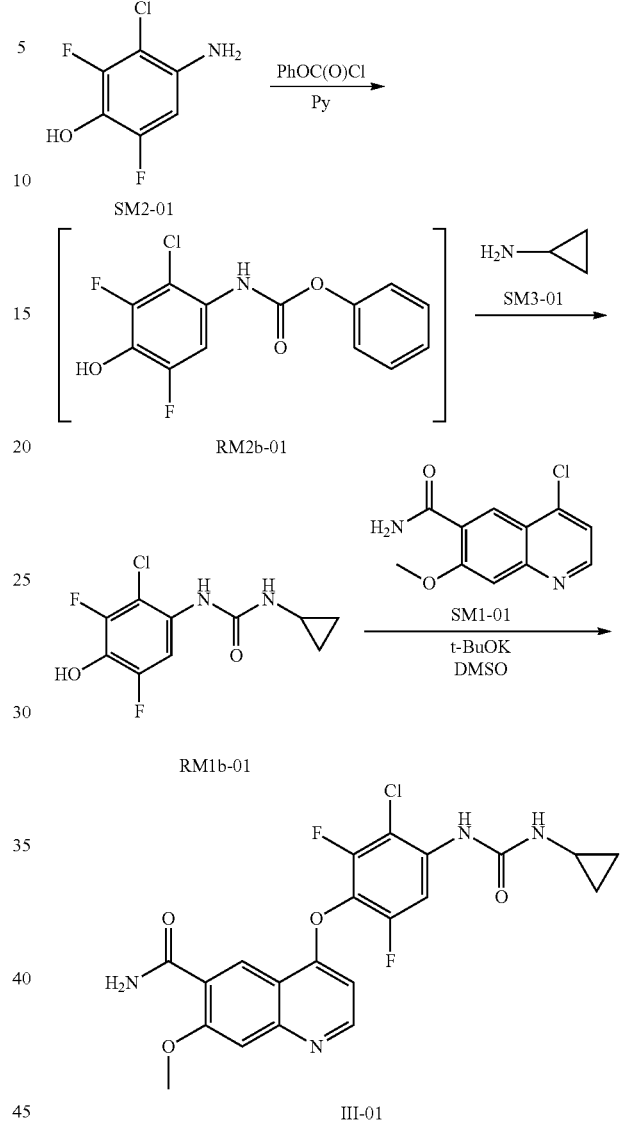

In the above method 1: the definition of E, G1, G2, G3, G4, G5, R1, R2, R3, X1, X2, X3, X4 is the same as the E, G1, G2, G3, G4, G5, R1, R2, R3, X1, X2, X3, X4 in claims 1-5, wherein, Base-1 is potassium tert-butoxide, Sol-1 is DMSO, Base-2 is pyridine, Sol-2 is DMF, Base-3 is cyclopropylamine, Sol-3 is MeCN.

The synthetic method 2 for each reaction step is as follows:

2.1 Synthesis of Intermediate RM1b 2.1-1 A mixture of SM2 (1.0 eq), Py (1.3 eq) and DMF (10×) was stirred in the ice bath. Phenyl chloroformate (1.1 eq) was added dropwise below 10° C. After the reaction was completed (IPC by HPLC), the reaction was worked up to get the RM2b or to the next step directly.

2.1-2 Cyclopropylamine (4.0 eq) was added dropwise below 10° C. Then the mixture was stirred at room temperature until the reaction was completed (IPC by HPLC). Acetonitrile (15~20×) was added to the mixture, and the appeared precipitate was filtered. 6N—HCl was added dropwise to a mixture of the precipitate (1×) and MeOH (4×). The mixture was stirred until fully soluble, and then water (12×) was added. Then the appeared precipitate was filtered, washed with water (4×) and dried to obtain intermediate RM1b.

2.2 Synthesis of the Target Product of III

A mixture of SM1 (1.0 eq), SM1b (1.0 eq-1.5 eq), DMSO (60 mL) and potassium t-butoxide (t-BuOK, 1.0~1.5 eq) was stirred at 40~100° C. After the reaction was completed (IPC by HPLC), the cooled mixture was dropped into ice water (100×). The appeared precipitate was filtered, washed by water and dried to obtain the target formula III product.

The following process is another example for preparation of the formula III compound III-01:

Synthetic Method 2a: Synthesis of the Formula III Compound III-01

2a.1 Synthesis of Intermediate RM1-01

2a.1-1: A mixture of SM2-01 (1.0 eq), Py (1.3 eq) and DMF (10×) was stirred in the ice bath. Phenyl chloroformate (1.1 eq) was added dropwise below 10° C. After the reaction was completed (IPC by HPLC), the reaction was worked up to get the RM2b-01 or to the next step directly.

2a.1-2: Cyclopropylamine (4.0 eq) was added dropwise below 10° C. Then the mixture was stirred at room temperature till the reaction was completed (IPC by HPLC). Acetonitrile (15~20×) was added to the mixture, and the appeared precipitate was filtered. 6N—HCl was added dropwise to a mixture of the precipitate (1×) and MeOH (4×). The mixture was stirred until fully soluble, and then water (12×) was added. Then the appeared precipitate was filtered, washed with water (4×) and dried to obtain intermediate RM1b-01.

2a.2 Synthesis of the Target Product of III-01

A mixture of SM1-01 (1.0 eq), SM1b (1.0~1.5 eq), DMSO (60 mL) and potassium t-butoxide (t-BuOK, 1.0~1.5 eq) was stirred at 40~100° C. After the reaction was completed (IPC by HPLC), the cooled mixture was dropped into ice water (100×). The appeared precipitate was filtered, washed by water and dried to obtain the formula III compound III-01.

Based on the preparation process described above, different kinds of the formula III products were prepared with different kinds of starting materials SM1, SM2 and SM3 as listed in Tables 1, 2, 4, and different kinds of intermediates RM1 and RM2 were prepared and listed in Table 3, and final formula III products are listed in Table 5, respectively, as follows:

TABLE 1

Starting Materials SM1

[Structure SM1-01]
[Structure SM1-02]
[Structure SM1-03]

TABLE 2

Starting Materials SM2

[Structure SM2-01]
[Structure SM2-02]

TABLE 2-continued

Starting Materials SM2

[Structure SM2-03]
[Structure SM2-04]
[Structure SM2-05]
[Structure SM2-06]
[Structure SM2-07]
[Structure SM2-08]
[Structure SM2-09]

TABLE 2-continued
Starting Materials SM2
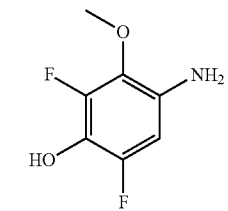
SM2-10
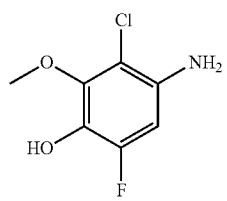
SM2-11
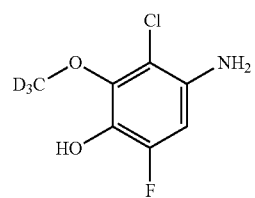 [SMILES: [2H]C([2H])([2H])Oc1c(O)c(F)cc(N)c1Cl]
SM2-12
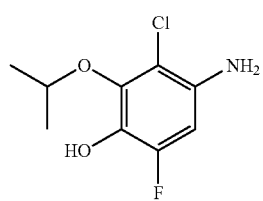
SM2-13
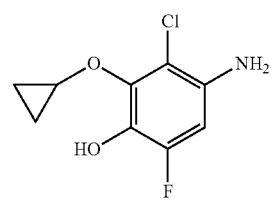 [SMILES: Nc1cc(F)c(O)c(OC2CC2)c1Cl]
SM2-14
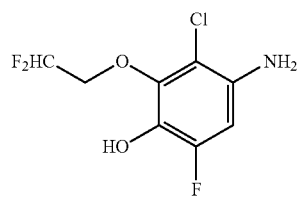 [SMILES: Nc1cc(F)c(O)c(OCC(F)F)c1Cl]
SM2-15
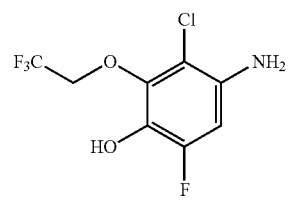 [SMILES: Nc1cc(F)c(O)c(OCC(F)(F)F)c1Cl]
SM2-16
TABLE 2-continued
Starting Materials SM2
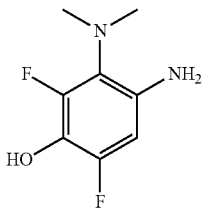
SM2-17
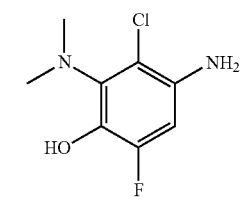
SM2-18
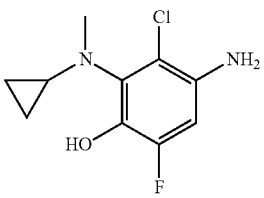
SM2-19
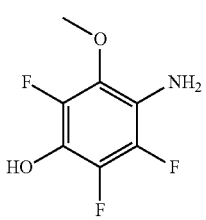
SM2-20
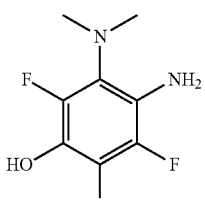
SM2-21
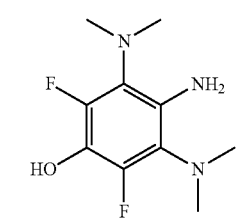
SM2-22

TABLE 3a
"RM1" Structure in the First Step of Synthetic Method I
RM1-01
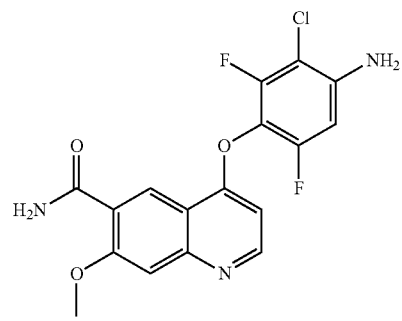
RM1-02
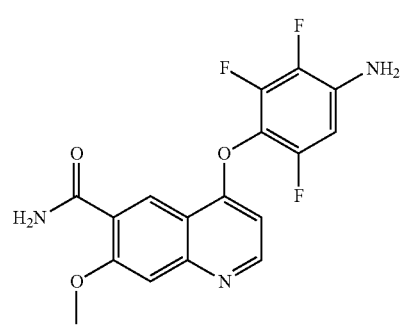 [SMILES: COc1cc2nccc(Oc3c(F)cc(N)c(F)c3F)c2cc1C(N)=O]
RM1-03
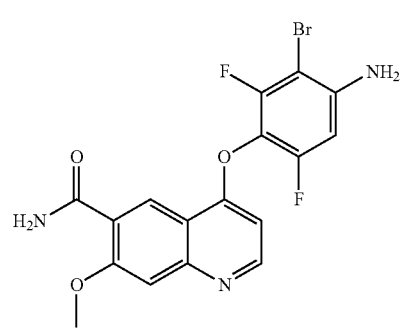 [SMILES: COc1cc2nccc(Oc3c(F)cc(N)c(Br)c3F)c2cc1C(N)=O]
RM1-04
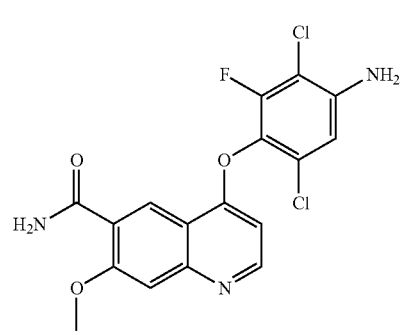 [SMILES: COc1cc2nccc(Oc3c(Cl)cc(N)c(Cl)c3F)c2cc1C(N)=O]
RM1-05
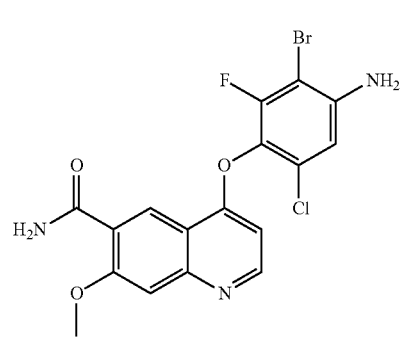 [SMILES: COc1cc2nccc(Oc3c(Cl)cc(N)c(Br)c3F)c2cc1C(N)=O]
TABLE 3a-continued
"RM1" Structure in the First Step of Synthetic Method I
RM1-06
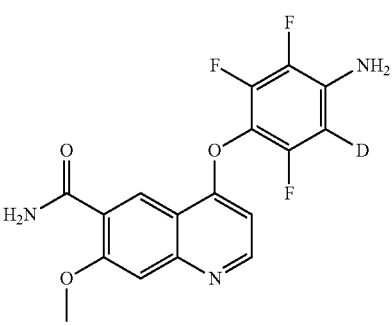 [SMILES: [2H]c1c(N)c(F)c(F)c(Oc2ccnc3cc(OC)c(C(N)=O)cc23)c1F]
RM1-07
RM1-08
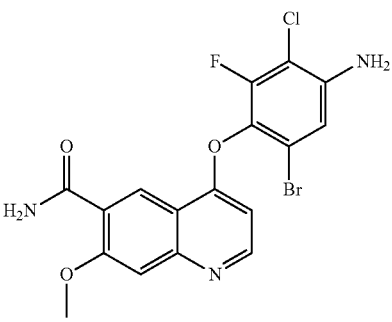 [SMILES: COc1cc2nccc(Oc3c(Br)cc(N)c(Cl)c3F)c2cc1C(N)=O]
RM1-09

TABLE 3a-continued
"RM1" Structure in the First Step of Synthetic Method I
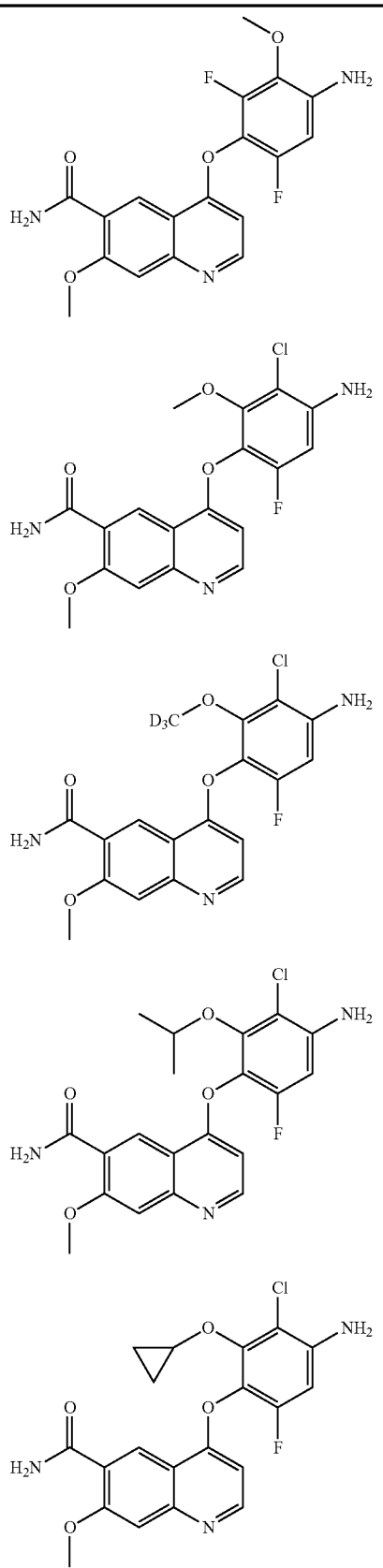
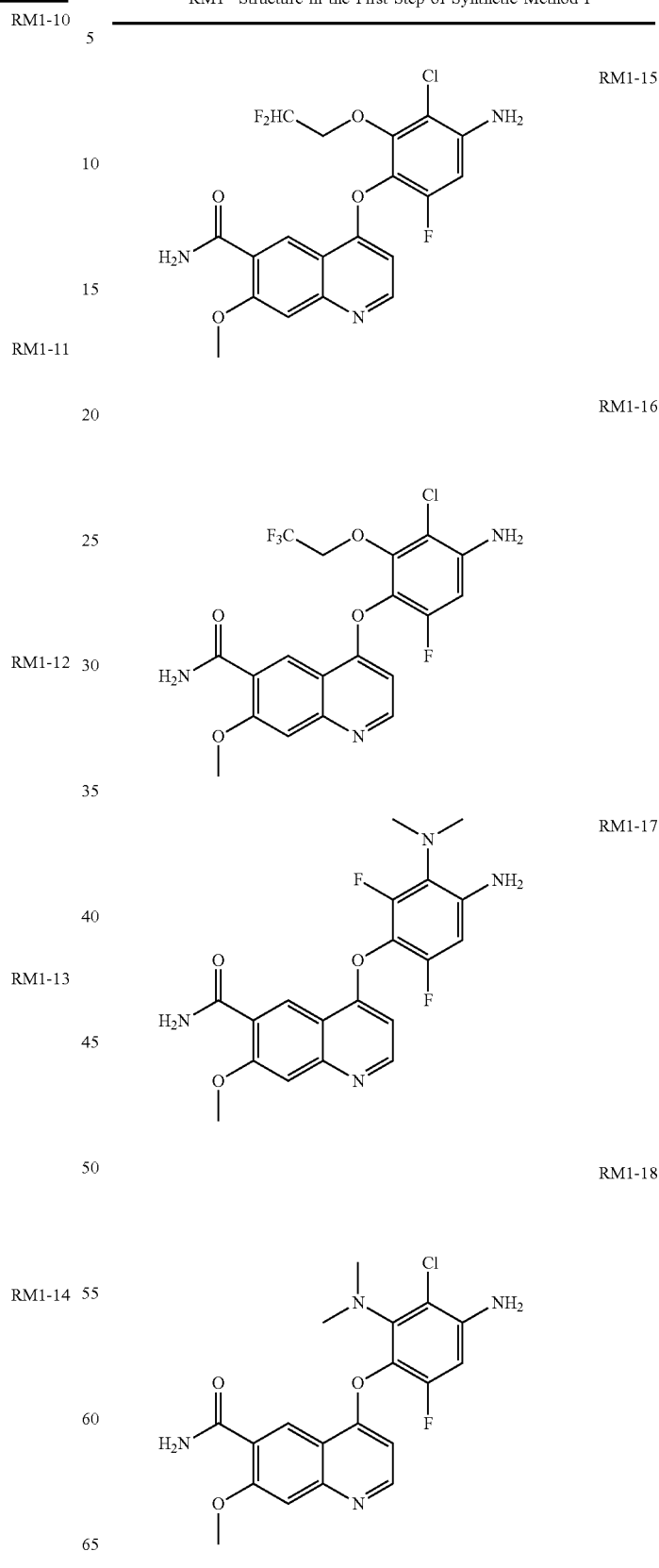

TABLE 3a-continued
"RM1" Structure in the First Step of Synthetic Method I
RM1-19
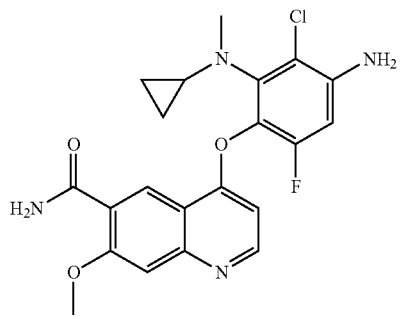 [SMILES: COc1cc2nccc(Oc3c(F)cc(N)c(Cl)c3N(C)C3CC3)c2cc1C(N)=O]
RM1-20
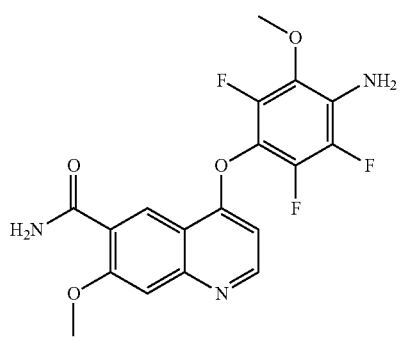 [SMILES: COc1cc2nccc(Oc3c(F)c(F)c(N)c(OC)c3F)c2cc1C(N)=O]
RM1-21
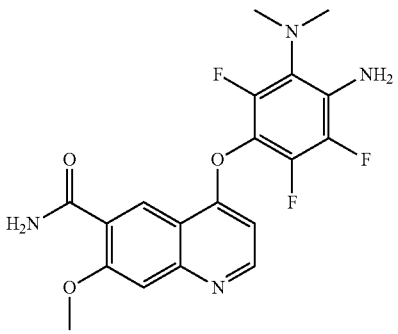 [SMILES: COc1cc2nccc(Oc3c(F)c(F)c(N)c(N(C)C)c3F)c2cc1C(N)=O]
RM1-22
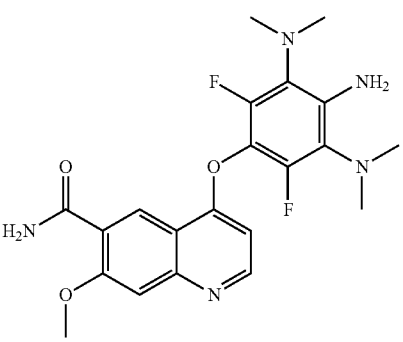 [SMILES: COc1cc2nccc(Oc3c(F)c(N(C)C)c(N)c(N(C)C)c3F)c2cc1C(N)=O]
TABLE 3b
"RM2" Structure in the Second Step of Synthetic Method I
RM2-01
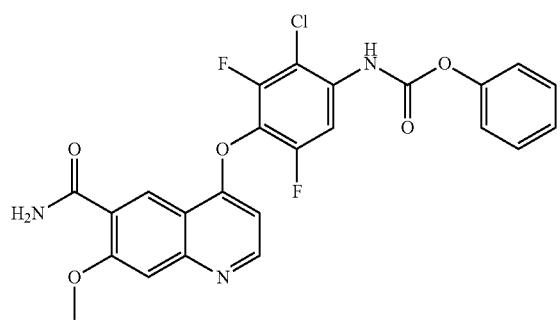
RM2-02
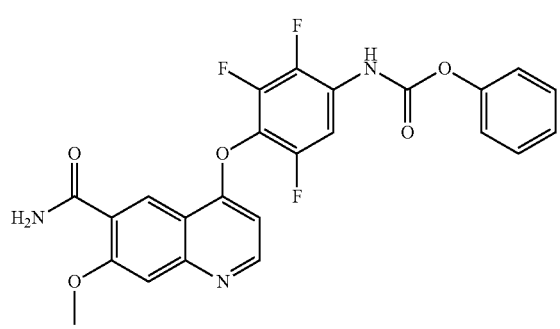 [SMILES: COc1cc2nccc(Oc3c(Cl)cc(NC(=O)Oc4ccccc4)c(F)c3F)c2cc1C(N)=O]

TABLE 3b-continued
"RM2" Structure in the Second Step of Synthetic Method I
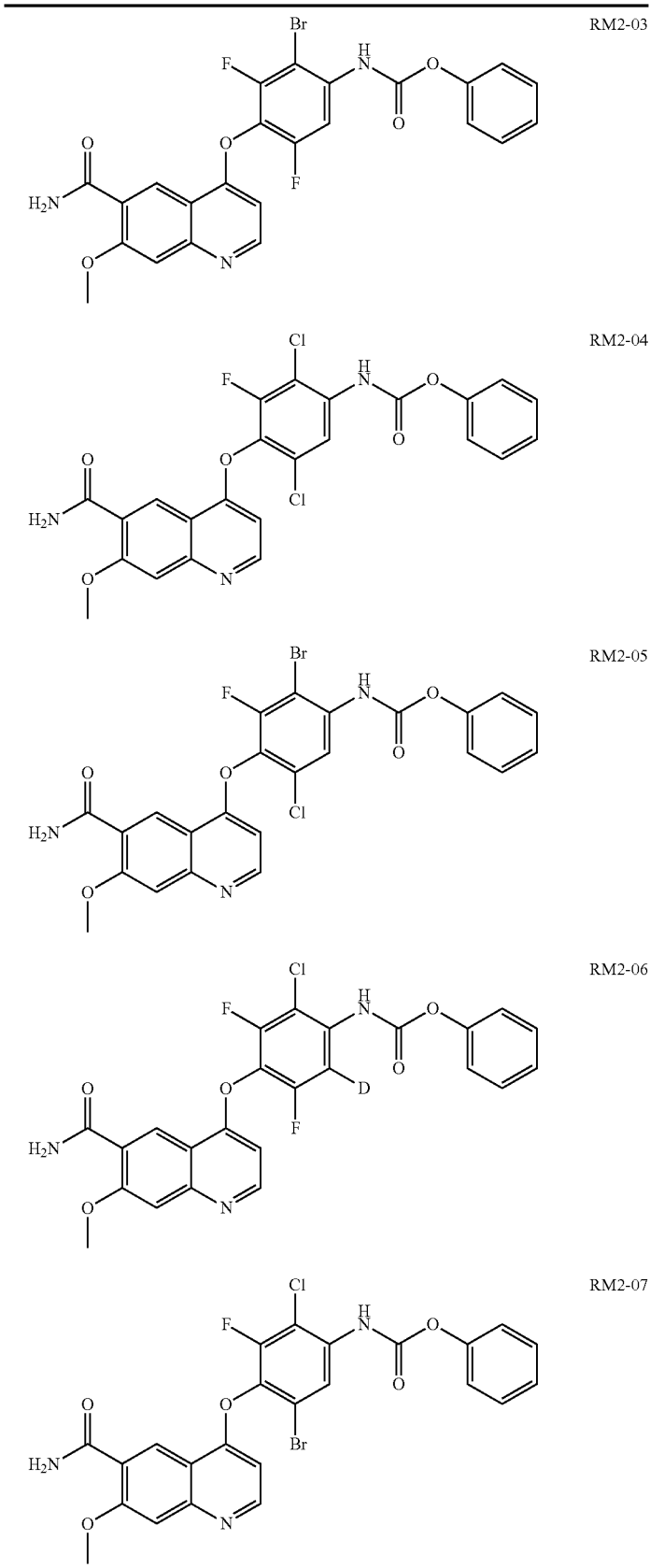
RM2-03
RM2-04
RM2-05
RM2-06
RM2-07

TABLE 3b-continued
"RM2" Structure in the Second Step of Synthetic Method I
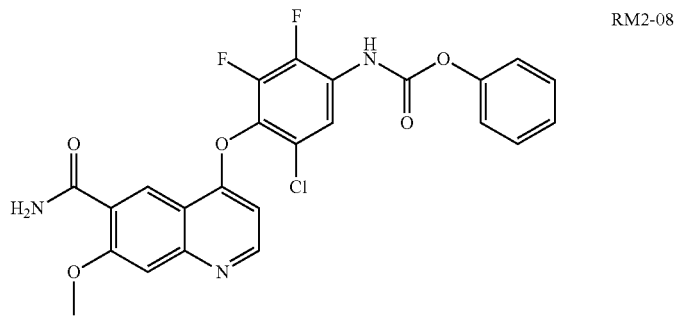
RM2-08
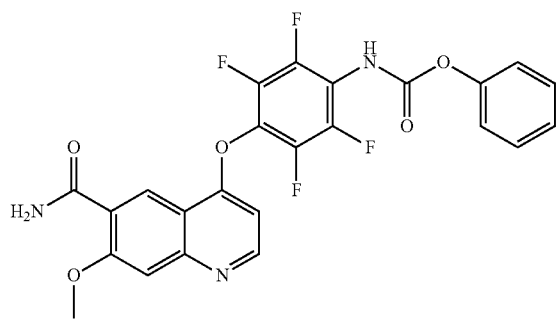 [SMILES: COc1cc2nccc(Oc3c(F)c(F)c(NC(=O)Oc4ccccc4)c(F)c3F)c2cc1C(N)=O]
RM2-09
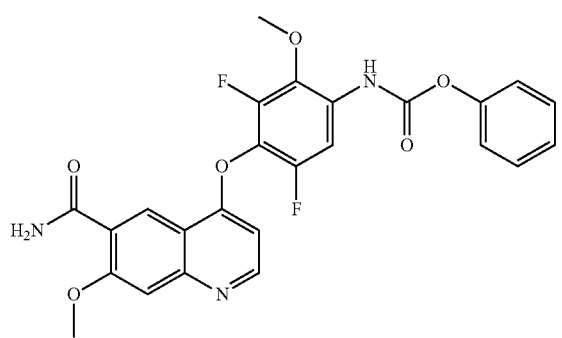 [SMILES: COc1cc2nccc(Oc3c(F)cc(NC(=O)Oc4ccccc4)c(OC)c3F)c2cc1C(N)=O]
RM2-10
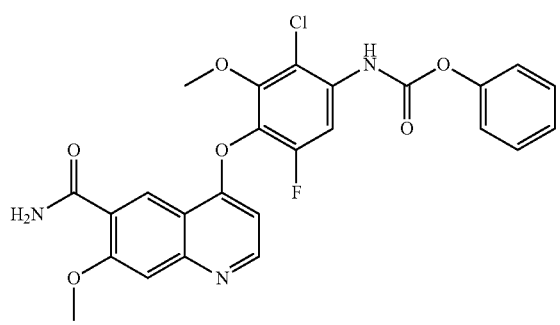 [SMILES: COc1cc2nccc(Oc3c(F)cc(NC(=O)Oc4ccccc4)c(Cl)c3OC)c2cc1C(N)=O]
RM2-11

TABLE 3b-continued
"RM2" Structure in the Second Step of Synthetic Method I
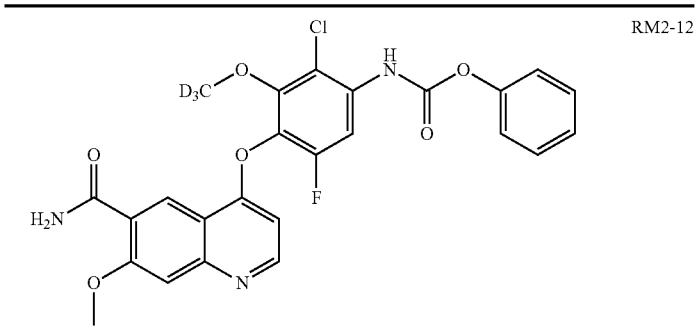
RM2-12
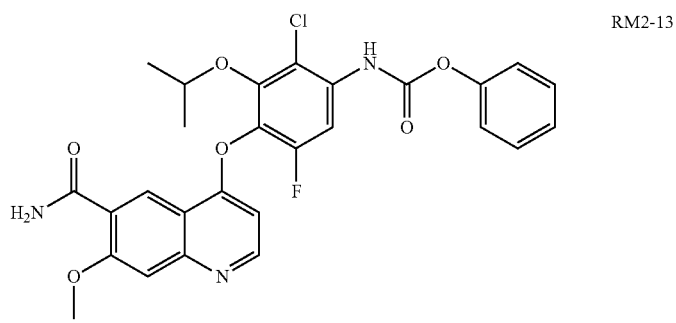
RM2-13
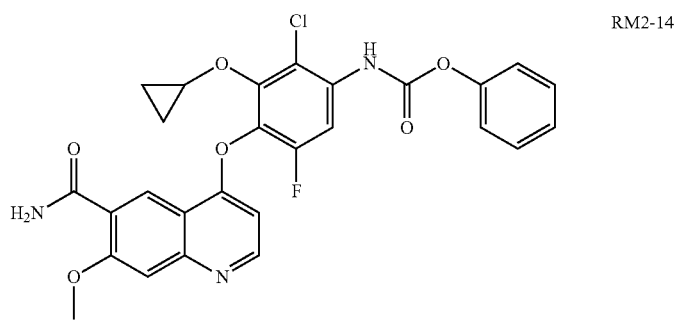
RM2-14
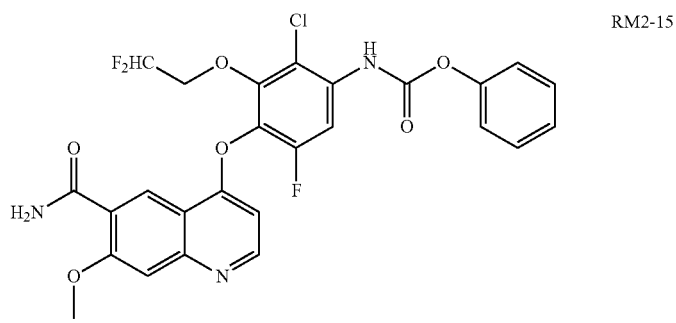
RM2-15
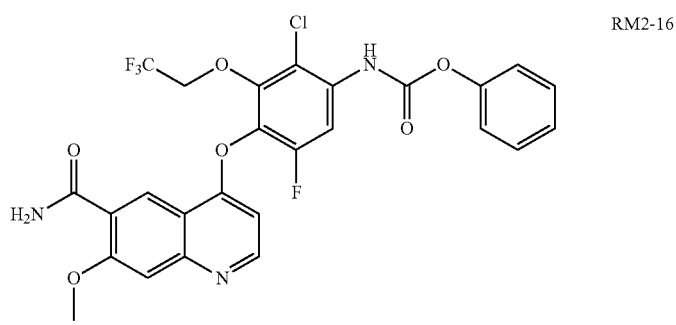
RM2-16

TABLE 3b-continued
"RM2" Structure in the Second Step of Synthetic Method I
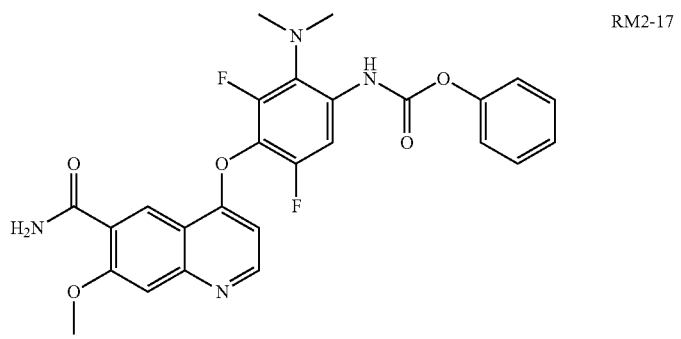
RM2-17
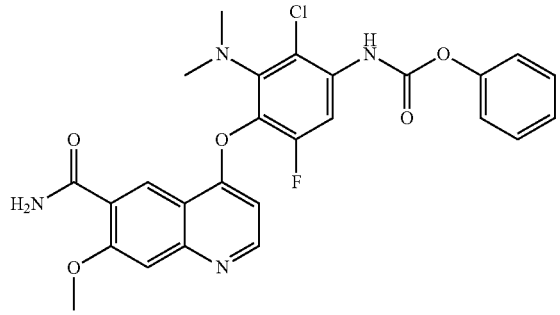 [SMILES: COc1cc2nccc(Oc3c(F)cc(NC(=O)Oc4ccccc4)c(Cl)c3N(C)C)c2cc1C(N)=O]
RM2-18
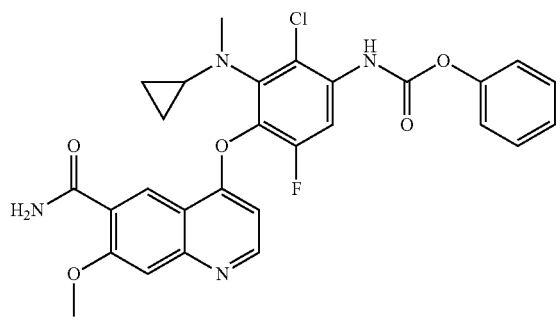 [SMILES: COc1cc2nccc(Oc3c(F)cc(NC(=O)Oc4ccccc4)c(Cl)c3N(C)C3CC3)c2cc1C(N)=O]
RM2-19
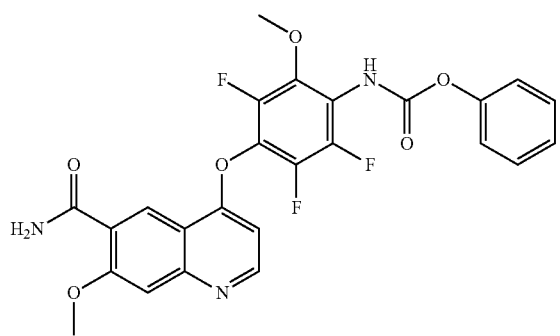 [SMILES: COc1cc2nccc(Oc3c(F)c(F)c(NC(=O)Oc4ccccc4)c(OC)c3F)c2cc1C(N)=O]
RM2-20

TABLE 3b-continued

"RM2" Structure in the Second Step of Synthetic Method I

RM2-21

RM2-22

TABLE 3c

"RM1b" Structure in the First Step of Synthetic Method 2

RM1b-01

RM1b-02

TABLE 4

Starting Materials SM3

SM3-01

SM3-02

TABLE 4-continued

Starting Materials SM3

SM3-03

SM3-04

SM3-05

SM3-06

SM3-07

SM3-08

SM3-09

TABLE 4-continued

Starting Materials SM3

| Structure | ID |
|---|---|
| H2N-CH(CH3)-CH2-OH (with stereochemistry) | SM3-10 |
| H2N-CH2-C(CH3)2-OH | SM3-11 |
| H2N-C(CH3)2-CH2-OH | SM3-12 |
| HOCH2-CH(NH2)-CH2OH | SM3-13 |
| H2N-CH2-CH(OH)-CH2OH (R) | SM3-14 |
| H2N-CH2-CH(OH)-CH2OH (S) | SM3-15 |
| isopropylamine | SM3-16 |
| 1-aminomethylcyclopropane (1-methyl-cyclopropylamine) | SM3-17 |
| 1-amino-2,2-difluorocyclopropane | SM3-18 |
| cyclopropylmethylamine | SM3-19 |
| cyclobutylamine | SM3-20 |
| 3-aminooxetane | SM3-21 |
| 4-aminotetrahydropyran | SM3-22 |
| cis-3-aminocyclobutanol | SM3-23 |
| (blank) | SM3-24 |
| trans-3-aminocyclobutanol | — |
| (R)-3-hydroxypyrrolidine | SM3-25 |
| (blank) | SM3-26 |
| (S)-3-hydroxypyrrolidine | — |
| 1-methylpiperazine | SM3-27 |
| (blank) | SM3-28 |
| 2-fluoroethylamine | — |
| 1-amino-N-cyclopropyl-2-vinylcyclopropane-1-carboxamide | SM3-29 |
| 1-amino-2,2,2-trifluoro-1-methylethane | SM3-30 |
| 1-amino-1-(trifluoromethyl)cyclopropane | SM3-31 |

TABLE 5
Formula III Product Structure Obtained by Synthetic Method 1 or 2
Structure of Formula III Products
III-01
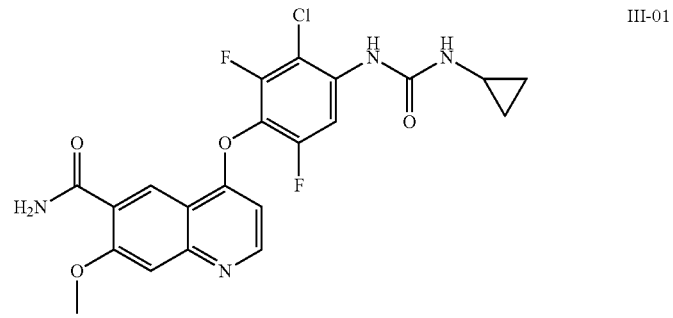
III-02
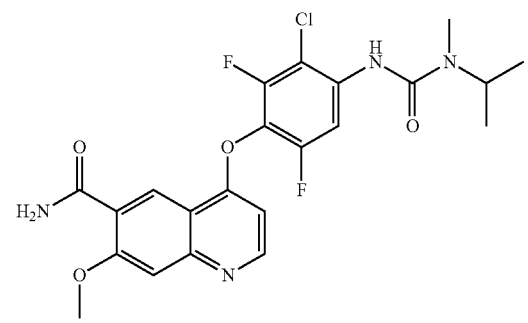 [SMILES: COc1cc2nccc(Oc3c(F)cc(NC(=O)N(C)C(C)C)c(Cl)c3F)c2cc1C(N)=O]
III-03
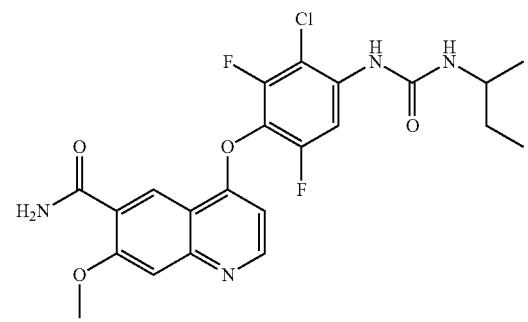 [SMILES: CCC(C)NC(=O)Nc1cc(F)c(Oc2ccnc3cc(OC)c(C(N)=O)cc23)c(F)c1Cl]
III-04
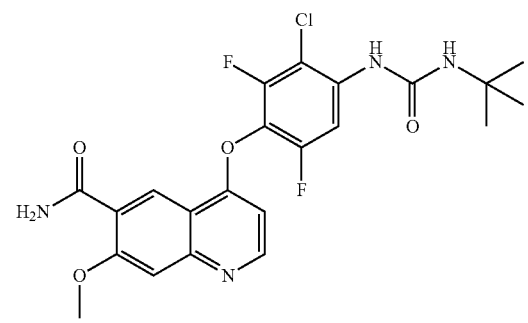 [SMILES: COc1cc2nccc(Oc3c(F)cc(NC(=O)NC(C)(C)C)c(Cl)c3F)c2cc1C(N)=O]

TABLE 5-continued
Formula III Product Structure Obtained by Synthetic Method 1 or 2
Structure of Formula III Products
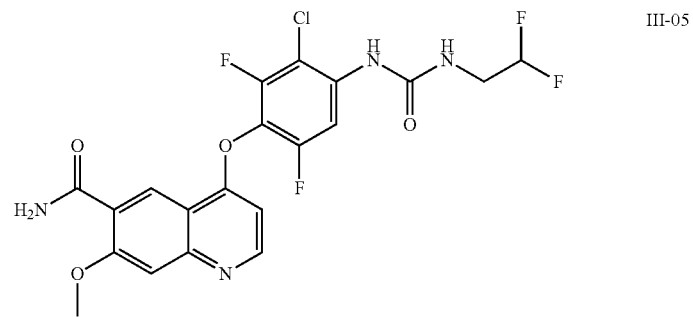
III-05
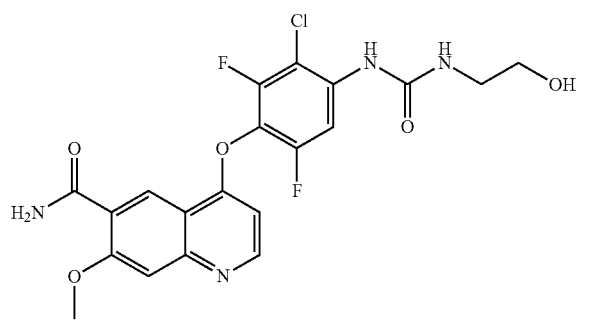 [SMILES: COc1cc2nccc(Oc3c(F)cc(NC(=O)NCCO)c(Cl)c3F)c2cc1C(N)=O]
III-06
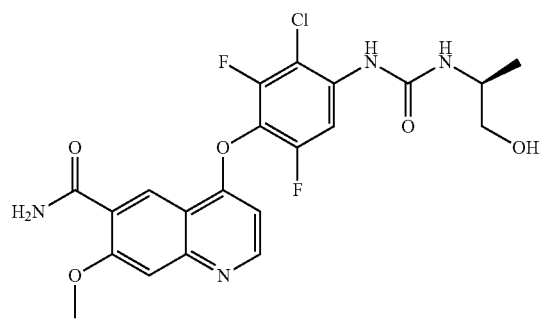 [SMILES: COc1cc2nccc(Oc3c(F)cc(NC(=O)N[C@@H](C)CO)c(Cl)c3F)c2cc1C(N)=O]
III-07
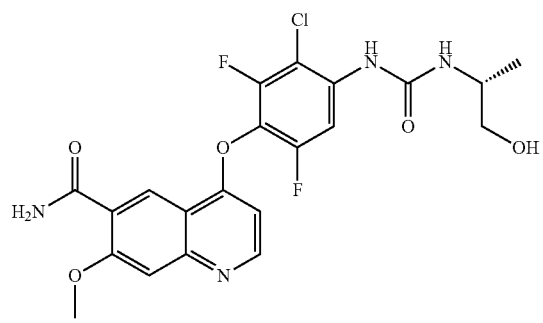 [SMILES: COc1cc2nccc(Oc3c(F)cc(NC(=O)N[C@H](C)CO)c(Cl)c3F)c2cc1C(N)=O]
III-08

TABLE 5-continued
Formula III Product Structure Obtained by Synthetic Method 1 or 2
Structure of Formula III Products
III-09
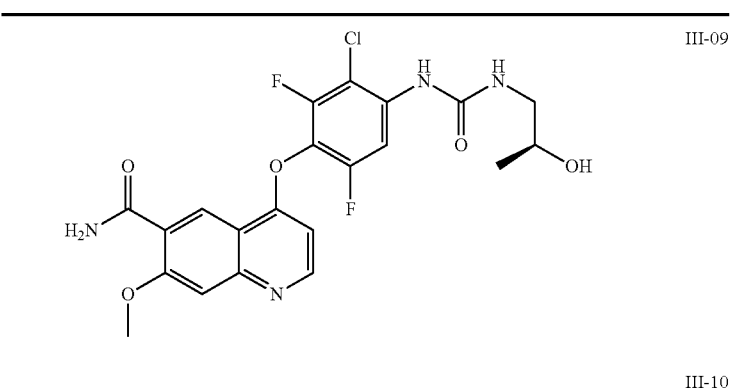
III-10
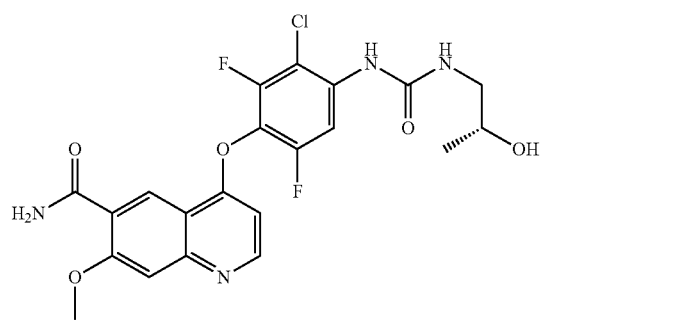 [SMILES: COc1cc2nccc(Oc3c(F)cc(NC(=O)NC[C@@H](C)O)c(Cl)c3F)c2cc1C(N)=O]
III-11
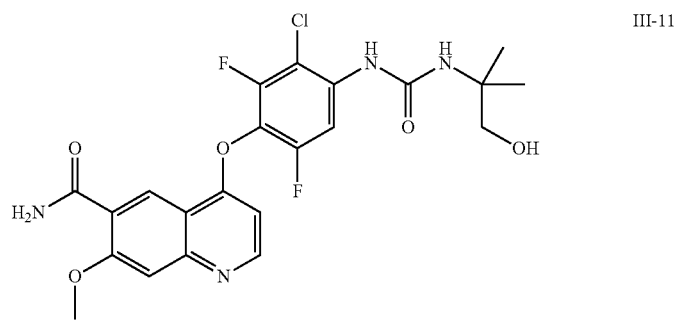
III-12
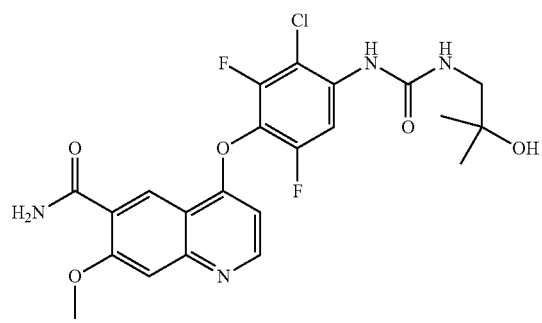 [SMILES: COc1cc2nccc(Oc3c(F)cc(NC(=O)NCC(C)(C)O)c(Cl)c3F)c2cc1C(N)=O]

TABLE 5-continued
Formula III Product Structure Obtained by Synthetic Method 1 or 2
Structure of Formula III Products
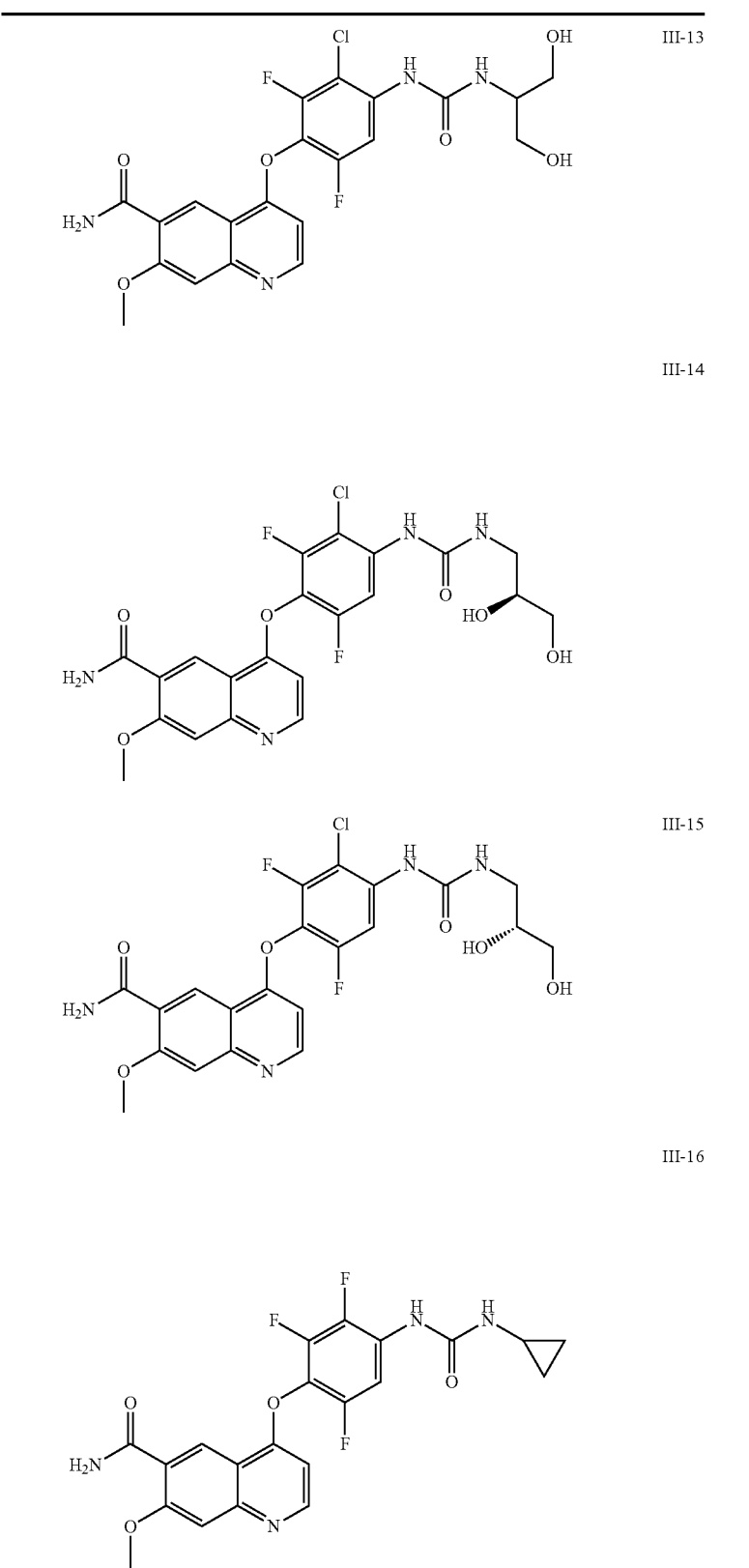

TABLE 5-continued
Formula III Product Structure Obtained by Synthetic Method 1 or 2
Structure of Formula III Products
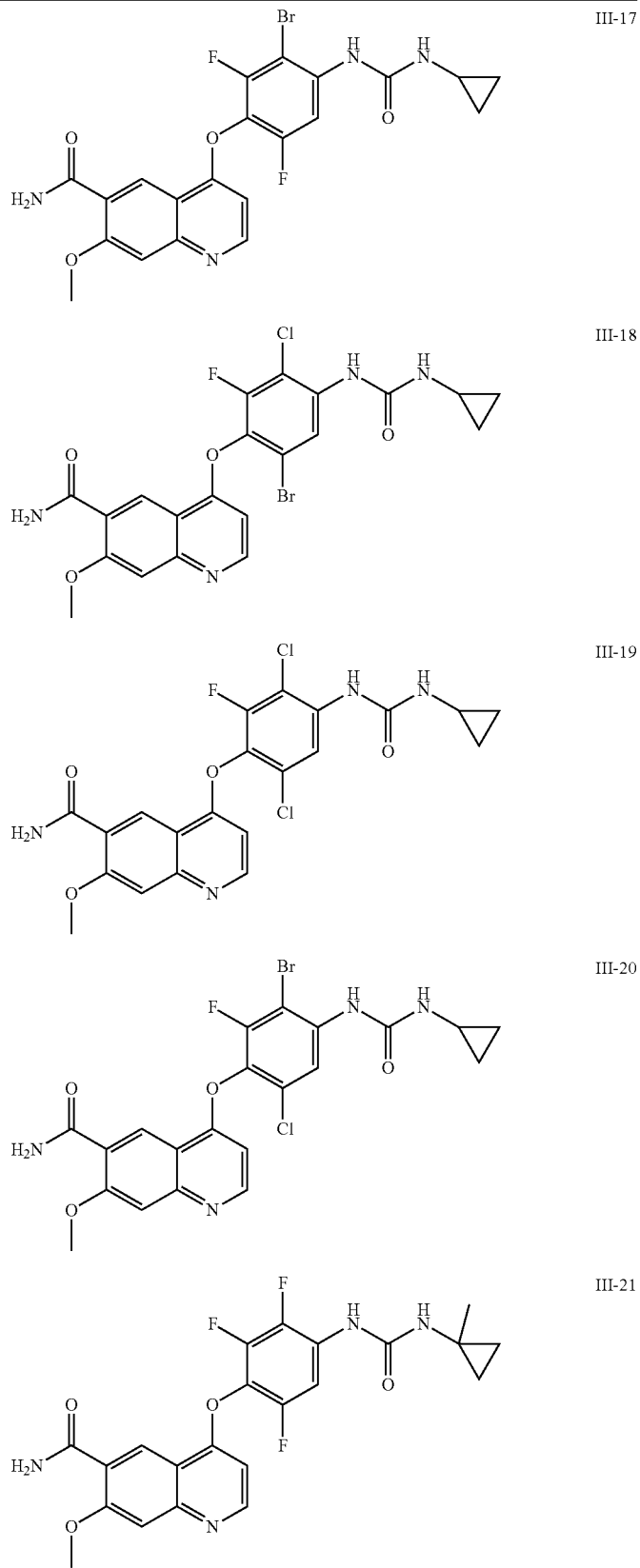
III-17
III-18
III-19
III-20
III-21

TABLE 5-continued
Formula III Product Structure Obtained by Synthetic Method 1 or 2
Structure of Formula III Products
III-22
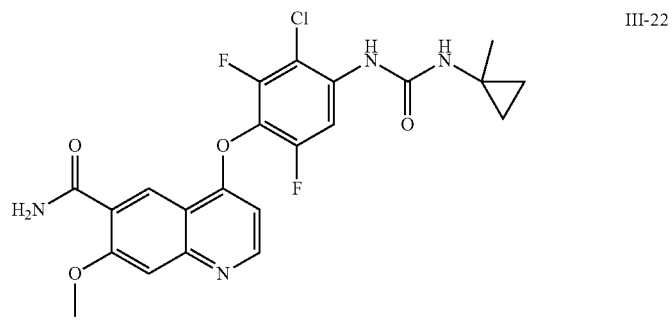
III-23
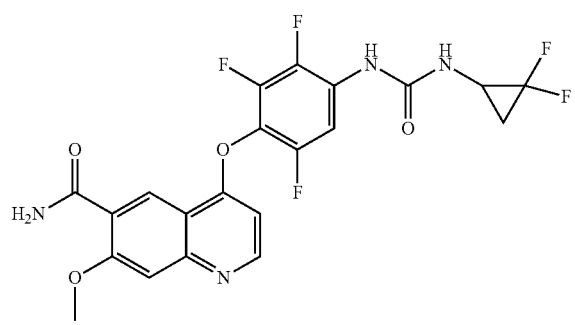 [SMILES: COc1cc2nccc(Oc3c(F)cc(NC(=O)NC4CC4(F)F)c(F)c3F)c2cc1C(N)=O]
III-24
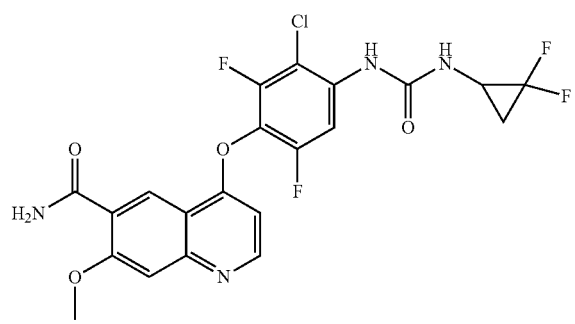 [SMILES: COc1cc2nccc(Oc3c(F)cc(NC(=O)NC4CC4(F)F)c(Cl)c3F)c2cc1C(N)=O]
III-25
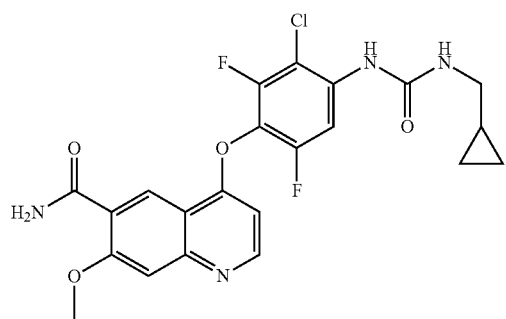 [SMILES: COc1cc2nccc(Oc3c(F)cc(NC(=O)NCC4CC4)c(Cl)c3F)c2cc1C(N)=O]

TABLE 5-continued
Formula III Product Structure Obtained by Synthetic Method 1 or 2
Structure of Formula III Products
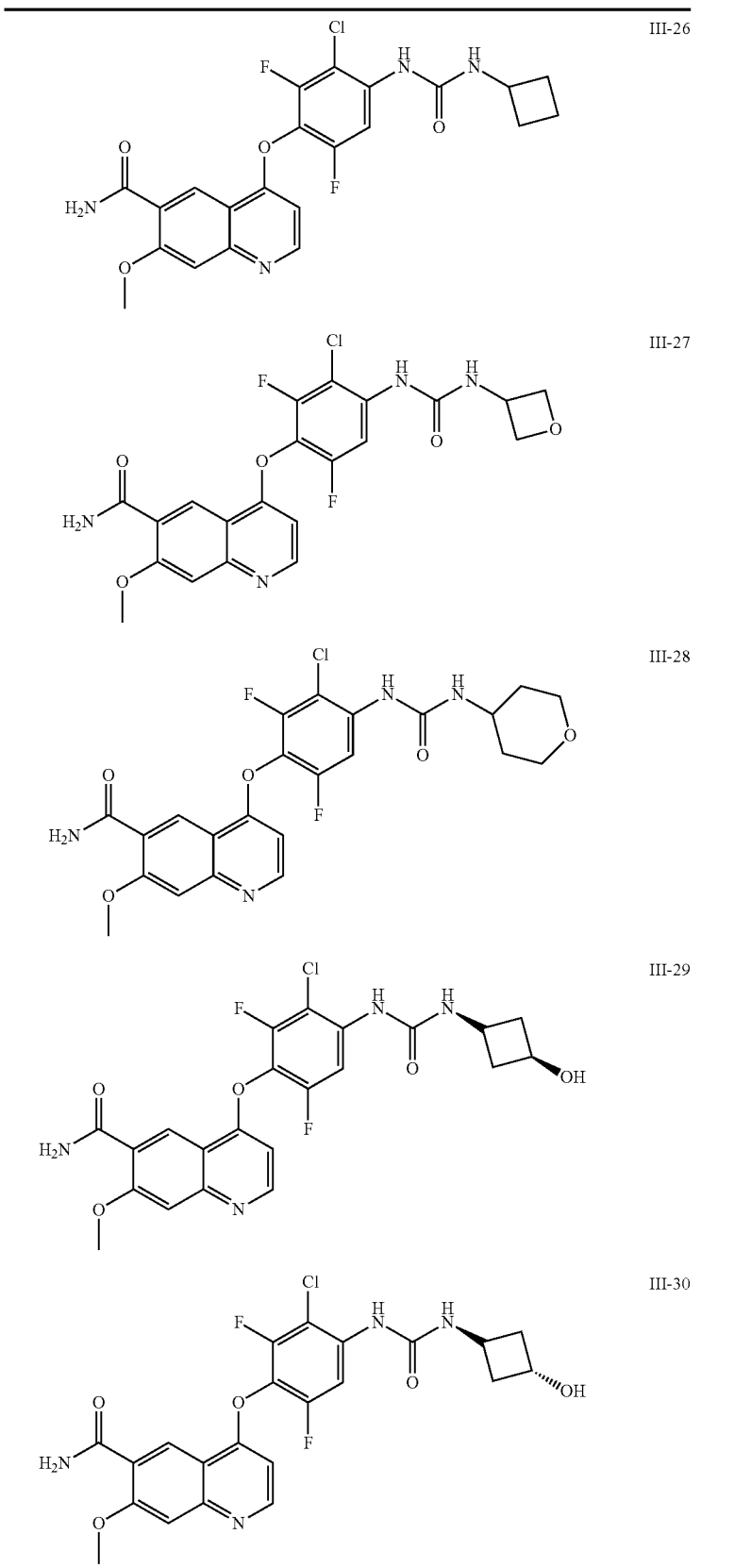

TABLE 5-continued
Formula III Product Structure Obtained by Synthetic Method 1 or 2
Structure of Formula III Products
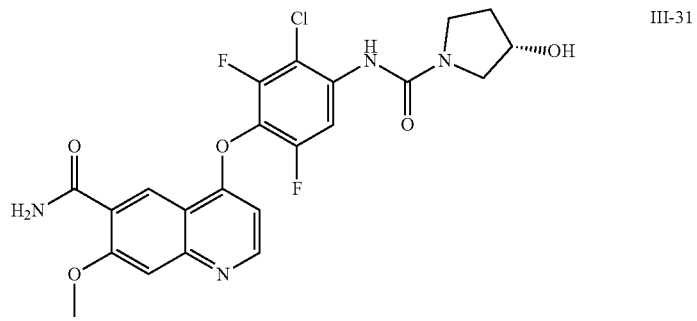
III-31
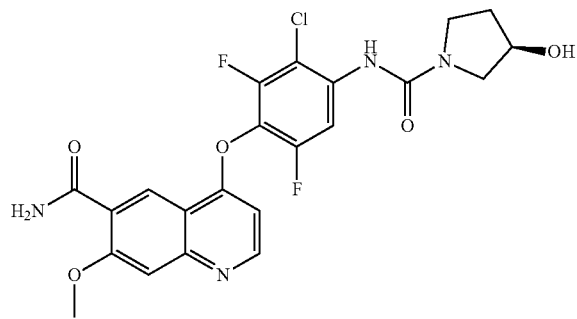 [SMILES: COc1cc2nccc(Oc3c(F)cc(NC(=O)N4CC[C@@H](O)C4)c(Cl)c3F)c2cc1C(N)=O]
III-32
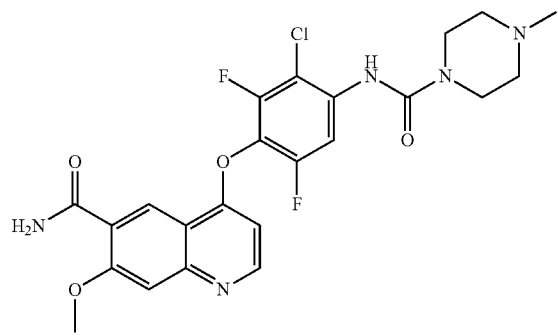 [SMILES: COc1cc2nccc(Oc3c(F)cc(NC(=O)N4CCN(C)CC4)c(Cl)c3F)c2cc1C(N)=O]
III-33
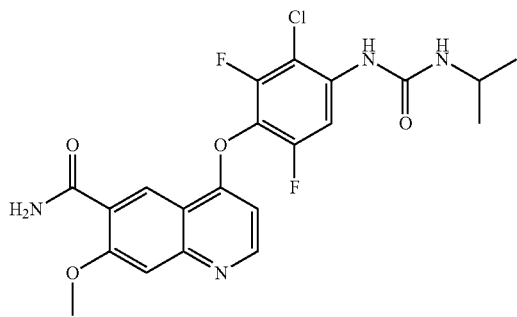 [SMILES: COc1cc2nccc(Oc3c(F)cc(NC(=O)NC(C)C)c(Cl)c3F)c2cc1C(N)=O]
III-34

TABLE 5-continued
Formula III Product Structure Obtained by Synthetic Method 1 or 2
Structure of Formula III Products
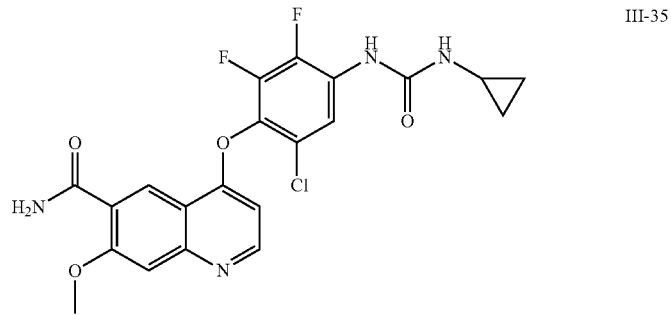
III-35
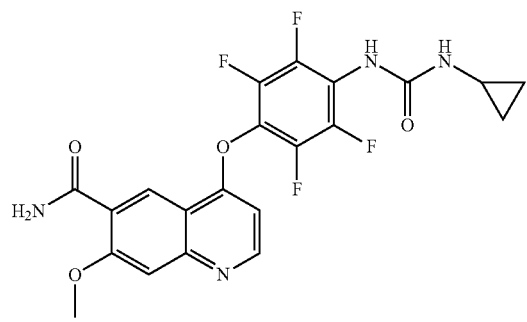 [SMILES: COc1cc2nccc(Oc3c(F)c(F)c(NC(=O)NC4CC4)c(F)c3F)c2cc1C(N)=O]
III-36
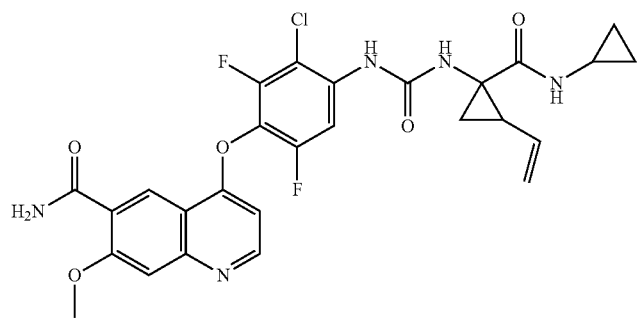 [SMILES: C=CC1CC1(NC(=O)Nc1cc(F)c(Oc2ccnc3cc(OC)c(C(N)=O)cc23)c(F)c1Cl)C(=O)NC1CC1]
III-37
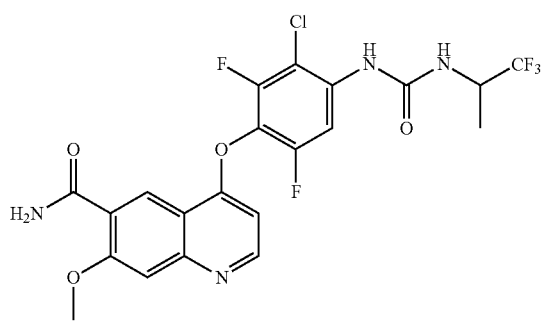 [SMILES: COc1cc2nccc(Oc3c(F)cc(NC(=O)NC(C)C(F)(F)F)c(Cl)c3F)c2cc1C(N)=O]
III-38

TABLE 5-continued
Formula III Product Structure Obtained by Synthetic Method 1 or 2
Structure of Formula III Products
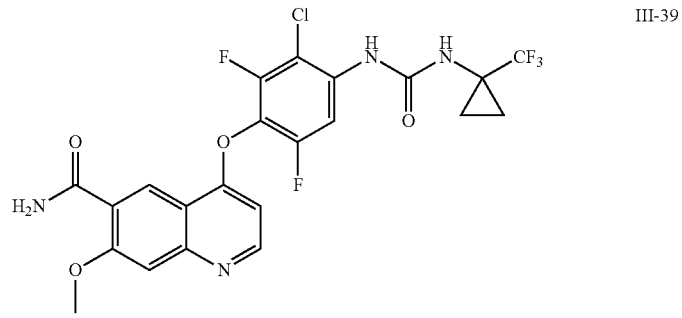
III-39
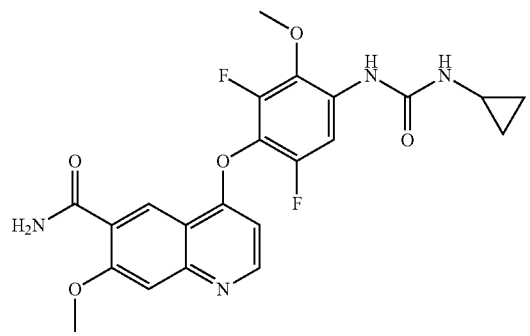
III-40
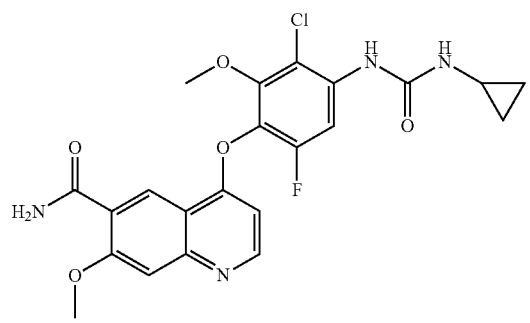
III-41
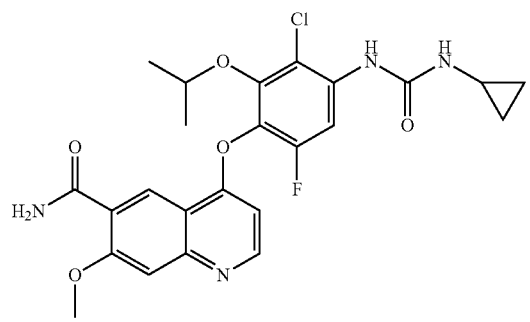 [SMILES: COc1cc2nccc(Oc3c(F)cc(NC(=O)NC4CC4)c(Cl)c3OC(C)C)c2cc1C(N)=O]
III-42

TABLE 5-continued
Formula III Product Structure Obtained by Synthetic Method 1 or 2
Structure of Formula III Products
III-43
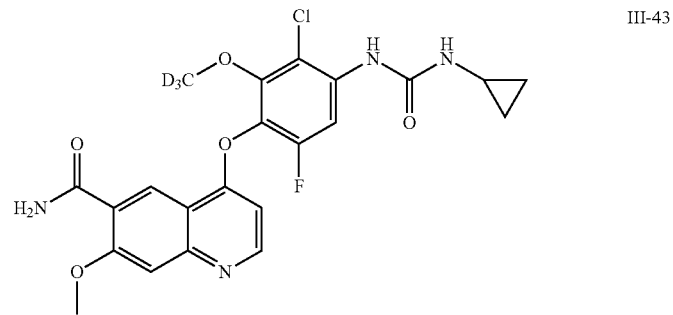
III-44
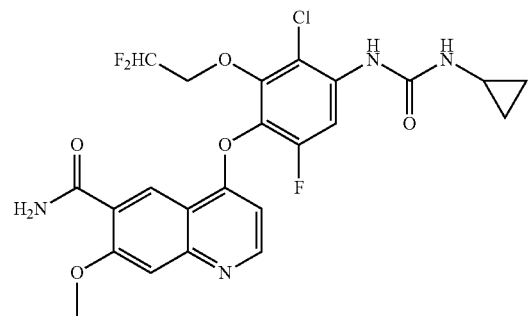 [SMILES: COc1cc2nccc(Oc3c(F)cc(NC(=O)NC4CC4)c(Cl)c3OCC(F)F)c2cc1C(N)=O]
III-45
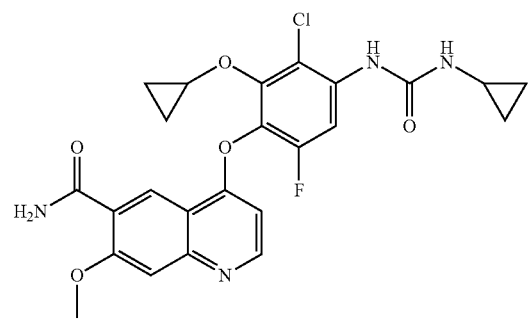 [SMILES: COc1cc2nccc(Oc3c(F)cc(NC(=O)NC4CC4)c(Cl)c3OC3CC3)c2cc1C(N)=O]
III-46
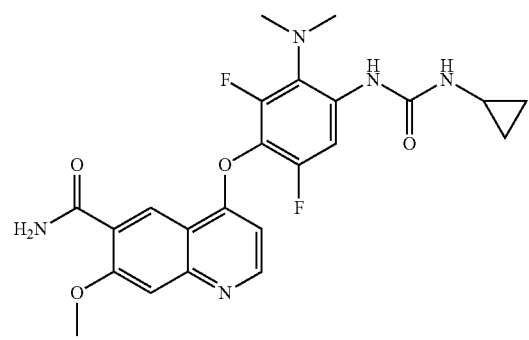 [SMILES: COc1cc2nccc(Oc3c(F)cc(NC(=O)NC4CC4)c(N(C)C)c3F)c2cc1C(N)=O]

TABLE 5-continued
Formula III Product Structure Obtained by Synthetic Method 1 or 2
Structure of Formula III Products
III-47
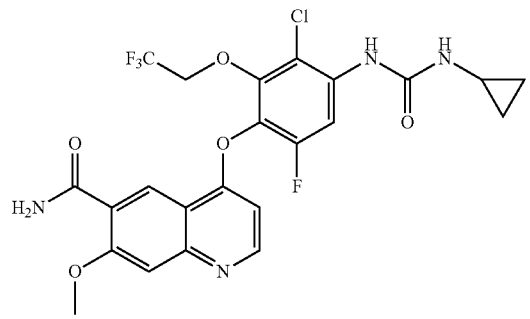 [SMILES: COc1cc2nccc(Oc3c(F)cc(NC(=O)NC4CC4)c(Cl)c3OCC(F)(F)F)c2cc1C(N)=O]
III-48
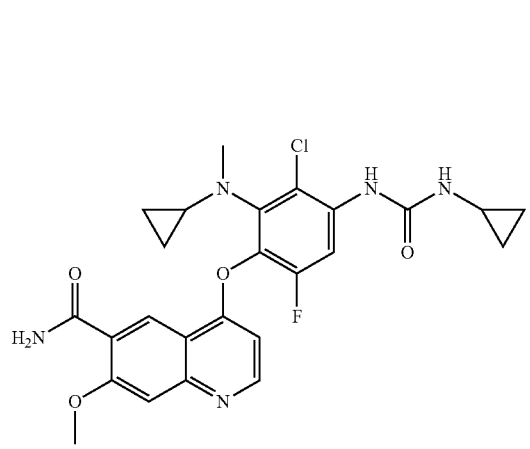
III-49
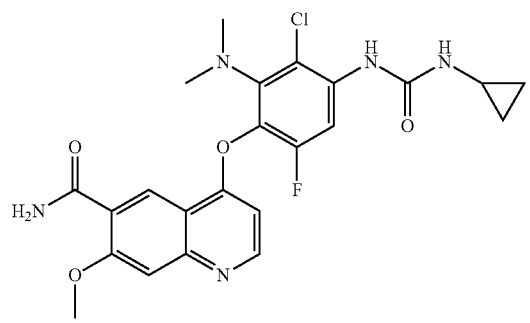 [SMILES: COc1cc2nccc(Oc3c(F)cc(NC(=O)NC4CC4)c(Cl)c3N(C)C)c2cc1C(N)=O]
III-50
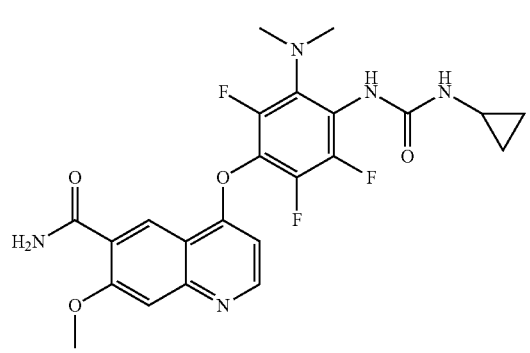 [SMILES: COc1cc2nccc(Oc3c(F)c(F)c(NC(=O)NC4CC4)c(N(C)C)c3F)c2cc1C(N)=O]

TABLE 5-continued

Formula III Product Structure Obtained by Synthetic Method 1 or 2
Structure of Formula III Products

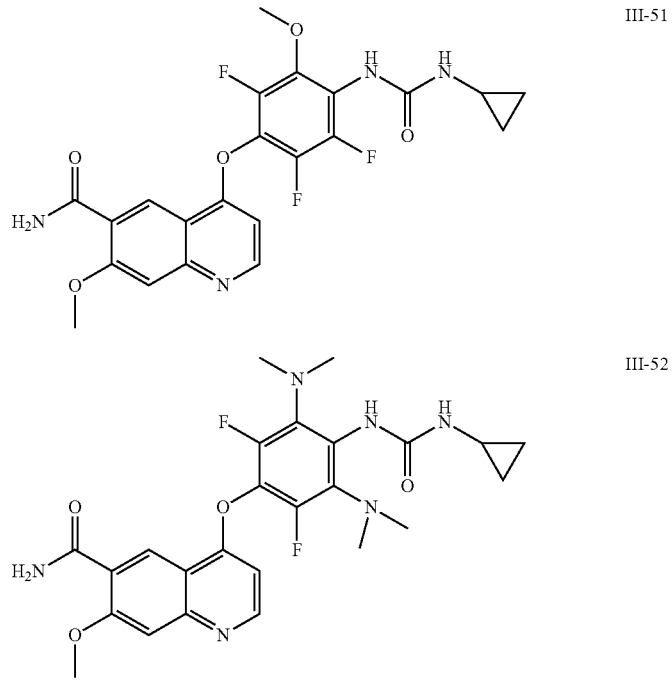

III-51

III-52

In the present invention, in addition to the synthesis of compounds III-01 to III-52 prepared in the corresponding Examples 1 to 52 by the above synthetic methods, it is also possible to synthesize some of the deuterated compounds listed in Table 5a below, which are prepared by using some deuterated reagents in which one or more of the hydrogens in SM1, SM2 and SM3 are replaced by deuterium isotopes, respectively, under the protection of a safety device. The compounds listed in Table 5a below can be synthesized under the protection of a safety device with some of the "H" of the compounds specified in claims 1 to 5 replaced by deuterium (D) isotopes (e.g., III-53, III-54, III-55, III-56, III-57, III-58, III-59, III-60, III-61, III-62, III-63, III-64, III-65, III-66, III-67, III-68, III-69) or compound III-70 in which all of the hydrogen (H) in III-01 is replaced by the deuterium (D) isotope.

TABLE 5a

Structure of Some Easily Deuterated Isotopic Formula III Compounds

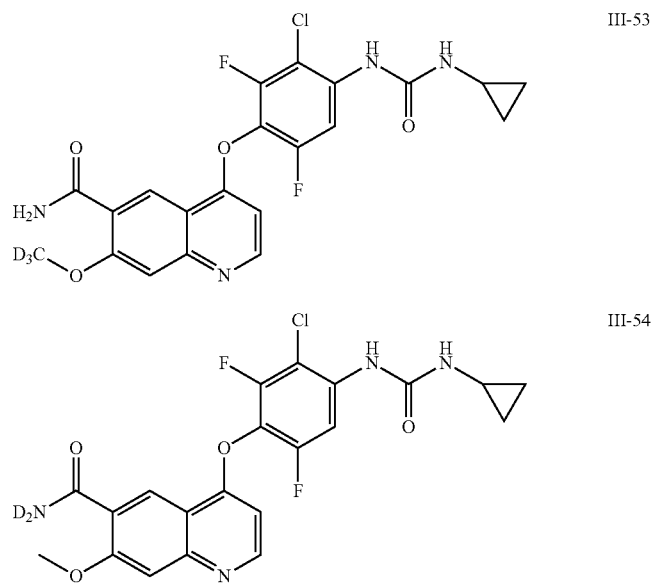

III-53

III-54

TABLE 5a-continued
Structure of Some Easily Deuterated Isotopic Formula III Compounds
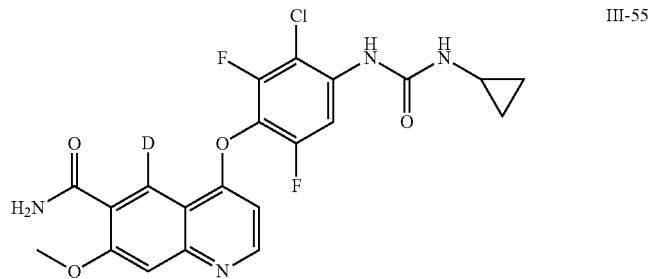
III-55
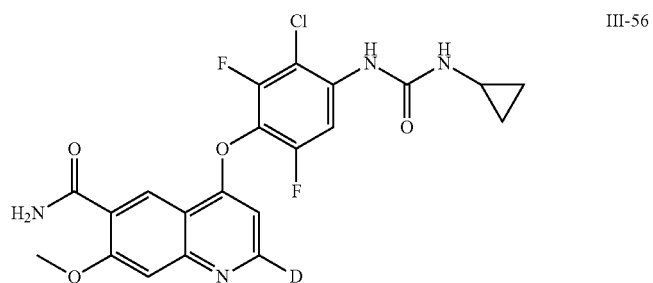
III-56
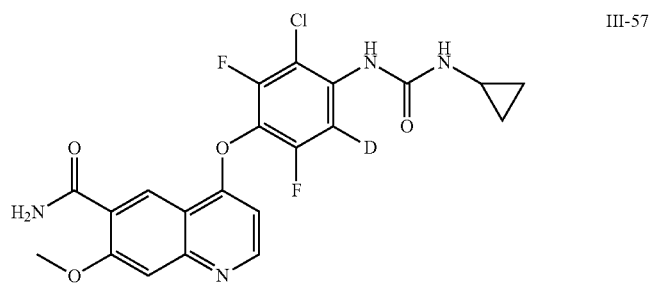
III-57
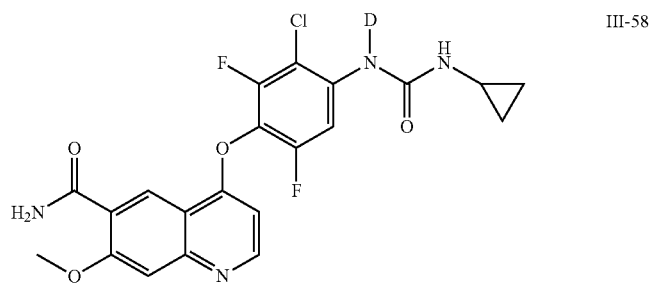
III-58
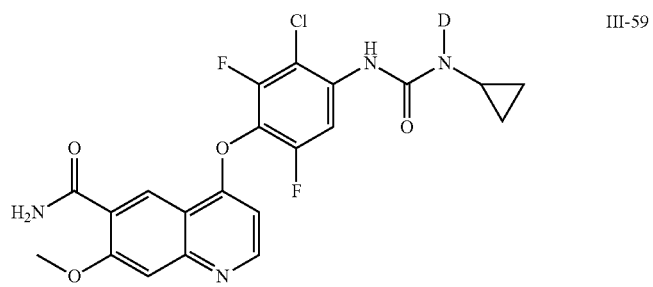
III-59

TABLE 5a-continued
Structure of Some Easily Deuterated Isotopic Formula III Compounds
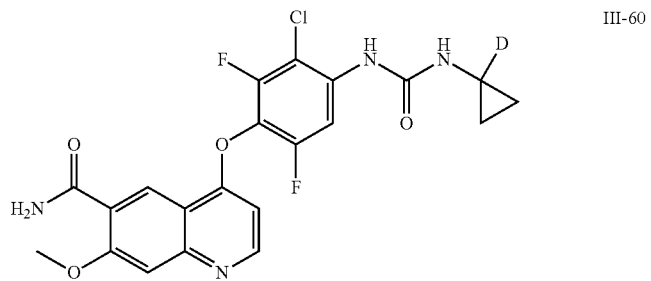
III-60
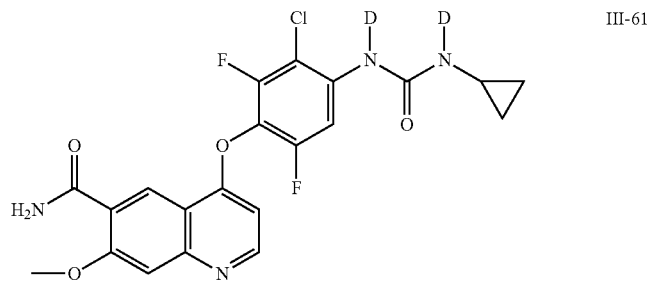
III-61
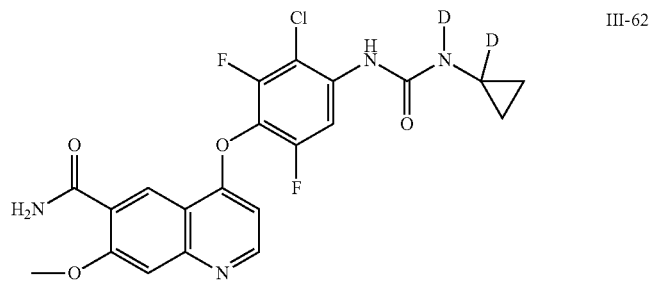
III-62
III-63
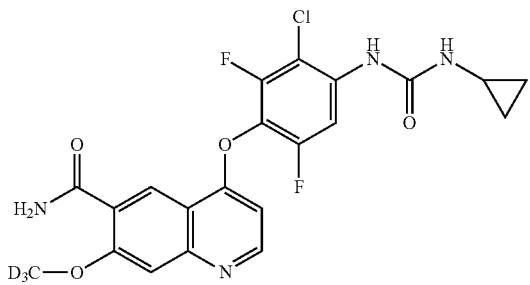 [SMILES: [2H]C([2H])([2H])Oc1cc2nccc(Oc3c(F)cc(NC(=O)NC4CC4)c(Cl)c3F)c2cc1C(N)=O]
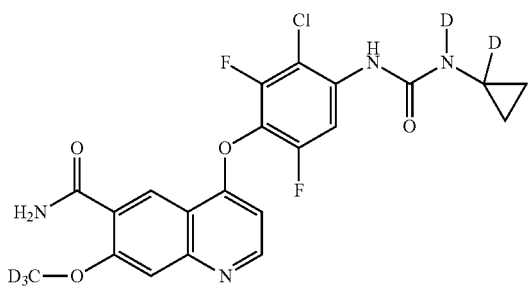
III-64

TABLE 5a-continued
Structure of Some Easily Deuterated Isotopic Formula III Compounds
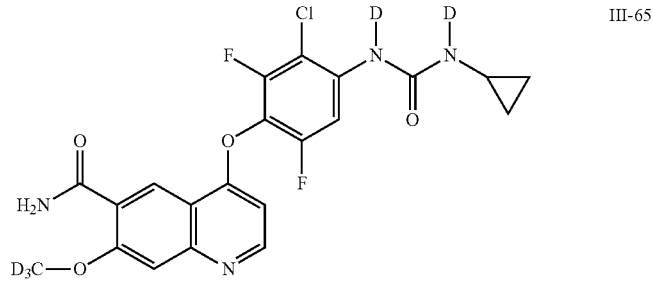
III-65
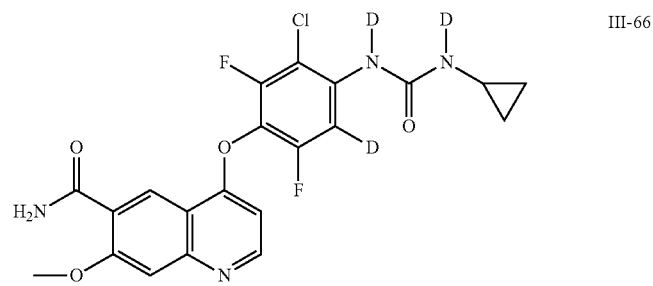
III-66
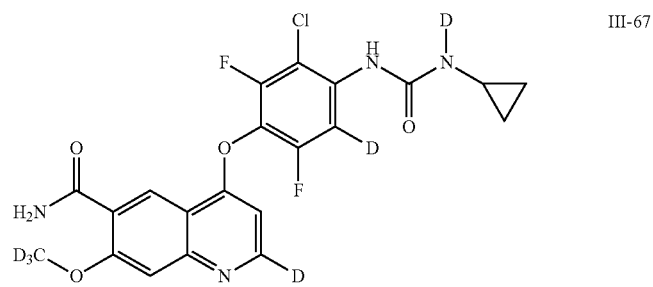
III-67
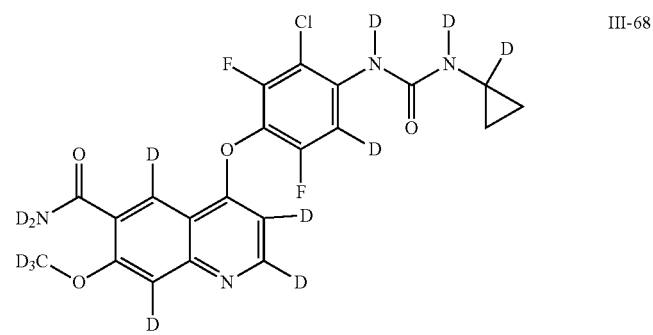
III-68
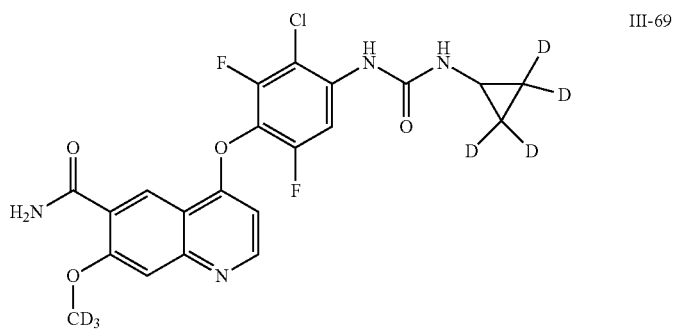
III-69

TABLE 5a-continued

Structure of Some Easily Deuterated Isotopic Formula III Compounds

III-70

Specific results concerning the synthesis and analysis of the novel compounds of formula III described above are detailed in the final embodiment of the present invention, and the structural characterization of each compound was determined by LC-MS and/or NMR ($^1$H-NMR, $^{13}$C-NMR and/or $^{19}$F-NMR) analysis, respectively.

In the following section were the detailed examples of the synthesis and biological activities of different kinds of compounds and their intermediates.

Instruments and Materials Related to Examples are as Follows

NMR ($^1$H-NMR, $^{13}$C-NMR and $^{19}$F-NMR spectra) were obtained from the analysis of an Ascend 400 m NMR instrument manufactured by Bruker. The chemical shifts were recorded with tetramethylsilane as internal standard, and the NMR analyses were all performed using deuterated DMSO, MeOH and other solvents, expressed in ppm (CHCl3: δ=7.26 ppm). The following data information was recorded: chemical shifts and their cleavage and coupling constants (s: single peak; d: double peak; t: triple peak; q: quadruple peak; br: broad peak; m: multiple peak).

The mass spectrometry data were analyzed using a liquid phase 1260 and mass spectrometry 6120 coupled by Agilent. The molecular weights of the compounds of formula III in the present invention were mainly in cationic mode ESI-MS [(M+H)$^+$].

The special raw materials and intermediates involved in this invention are provided by Shanghai Zannan Technology Co., Ltd. and other custom processing, and all other chemical reagents are purchased from Shanghai Reagent Company, Aldrich Company, Acros Company and other reagent suppliers. If the intermediates or products required for the reaction during the synthesis are not enough for the next step and other tests, the synthesis is repeated several times until sufficient quantities are available. The activity tests of the compounds prepared by the invention as well as pharmacological and toxicological tests were done by CRO service companies in Shanghai and Beijing according to industry regulations.

The abbreviations of the relevant chemical raw materials, reagents and solvents involved in the present invention and its embodiments are annotated as follows.
Boc: tert-Butoxycarbonyl
(Boc)$_2$O: Di-tert-butyl dicarbonate
CDI: N'-carbonyl diimidazole
DBU: 1,8-diazabicyclo[5.4.0]undec-7-ene
EDCI: N-ethyl-N'-(3-dimethylaminopropyl)carbodiimide hydrochloride
HATU: 2-(7-azobenzotriazole)-N,N,N',N'-tetramethyluronium hexafluorophos phate
NBS: N-bromosuccinimide
NCS: N-chlorosuccinimide
SOCl$_2$: Sulfoxide chloride
Pd/C: Palladium carbon
DIEA: N,N-diisopropylethylamine
DMAP: 4-Dimethylaminopyridine
HMTA: Hexamethylenetetramine
Py: Pyridine
HBr: Hydrobromic acid
HCl: Hydrochloric acid
HOAc: Glacial acetic acid
TFA: Trifluoroacetic acid
MsOH: Methanesulfonic acid
TsOH: p-toluenesulfonic acid
Cs2CO3: Cesium carbonate
tBuOK: Potassium tert-butoxide
KOH: Potassium hydroxide
NaOH: Sodium hydroxide
LiOH: Lithium hydroxide
ACN/MeCN: Acetonitrile
DCM: Dichloromethane
DCE: Dichloroethane
DMF: N,N-dimethylformamide
DMSO: Dimethyl sulfoxide
Et2O: Diethyl ether
EA: Ethyl acetate
PE: Petroleum ether
THF: Tetrahydrofuran
TBME: methyl tert-butyl ether
Me: Methyl
Et: Ethyl
Pr: Propyl
iPr: Isopropyl
cPr: Cyclopropyl Ph: Phenyl The new multi-substituted functional compound SM2-01 and series of formula III compounds III-01 to III-52 were synthesized according to the relevant synthetic methods shown above, respectively.

Example 1

Synthesis of Compound SM2-01

Method 1 for Synthesis of Compound SM2-01

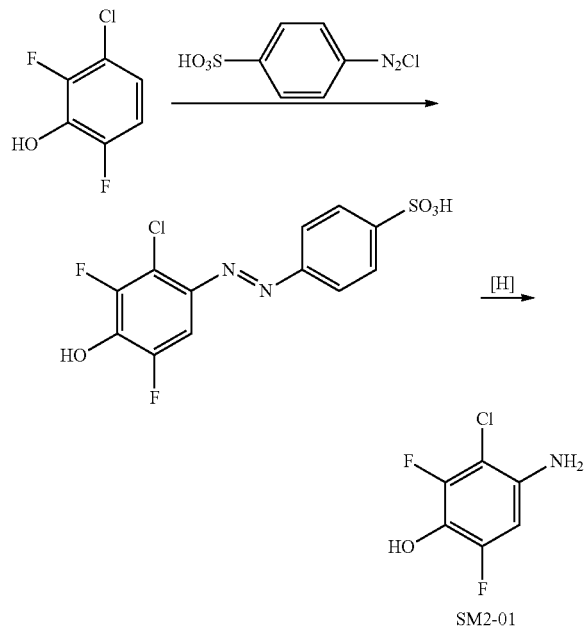

The solution of NaNO$_2$ (25 g in water 75 mL) was added dropwise to a mixture of p-aminobenzenesulfonic acid (60 g), water (500 mL) and Na$_2$CO$_3$ (20 g) in a 1 L three-mouth flask below 5° C. After the completion of adding the solution of NaNO$_2$, 12N—HCl was added dropwise to the mixture below 5° C. The mixture was stirred for 40 minutes for preparation of diazo salt of p-aminobenzenesulfonic acid.

The solution of diazo salt of p-aminobenzenesulfonic acid was added dropwise to a mixture of 3-Chloro-2,6-difluorophenol (44 g), water (516 g), 5N—NaOH (70 mL) and Na$_2$CO$_3$ (28 g) below 5° C. After the reaction was completed, pH was adjusted to 5.0 by adding 12N—HCl. Then ammonium formate (108 g) and Zn powder (65 g) was added the reaction mixture slowly. After the reaction was completed, the filtration was extracted with EA (500 mL×2) and the combined organic phase was washed with water and dried with anhydrous sodium sulfate. The solvent was removed and DCM (120 mL) was added to the slurry. After stirring, the appeared precipitate was filtered, washed and dried to give SM2-01 (40 g), yield: 83%.

$^1$H-NMR for the SM2-01 hydrochloride (400 MHz, CD$_3$OD) δ:7.30/7.273 (m, 1H);

$^{13}$C-NMR for the SM2-01 hydrochloride (100 MHz, CD$_3$OD) δ: 153.51 (m), 151.95 (m), 137.45 (m), 120.98 (m), 113.68 (m), 109.00 (m);

$^{19}$F-NMR for the SM2-01 hydrochloride (377 MHz, CD$_3$OD) δ: −132.36, −132.40, −133.09, −133.13.

ESI-MS (M+H$^+$): m/z calculated: 180.0, founded: 180.1.

Method 2 for Synthesis of Compound SM2-01

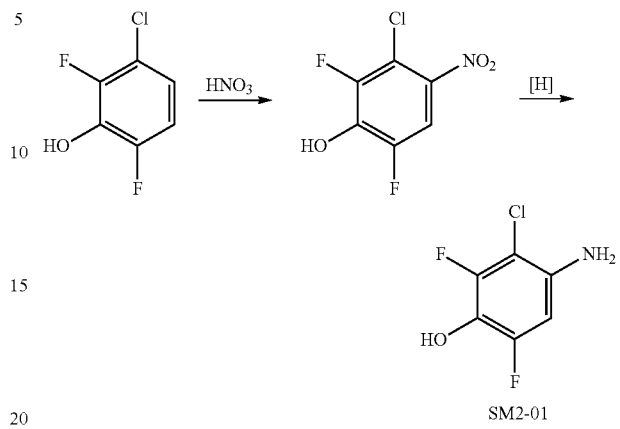

Concentrated nitric acid (300 g) was added dropwise to a mixture of 3-Chloro-2,6-difluorophenol (500 g) and DCM (2 L) below 10° C. After the reaction was completed, the mixture was extracted with DCM (1 L×2) and the combined organic phase was washed with water. and concentrated. The solvent was removed to give 3-chloro-2,6-difluoro-4-nitrophenol (675 g).

The powder of Fe (500 g) was added to a mixture of 3-chloro-2,6-difluoro nitrophenol (675 g) and H$_2$O (5.0 L). Then 12N—HCl (100 mL) was added dropwise to the mixture between 85° C. and 95° C. After the completion of adding 12N—HCl, The powder of Fe (500 g) was added. After the reaction was completed, the filtration was extracted with EA (2 L×2) and the combined organic phase was washed with water and dried with anhydrous sodium sulfate. The solvent was removed and DCM (600 mL) was added to the slurry. After stirring, the appeared precipitate was filtered, washed and dried to give SM2-01 (393 g), yield: 72%.

NMR and LC-MS analyses were confirmed that SM2-01 could be reliably synthesized by two methods, the key trihalogenated aminophenol compound in the innovation of the present invention.

Example 2

Synthesis of Compound III-01

Method 1 for Synthesis of Compound III-01

1.1 Synthesis of Compound RM1-01

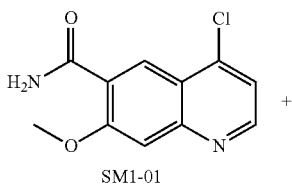

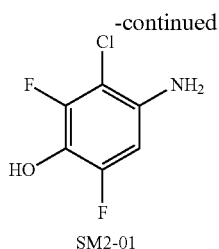

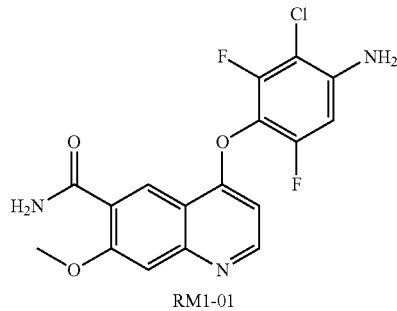

A mixture of SM1-01 (2.36 g, 10 mmol), SM2-01 (2.33 g, 13 mmol), potassium t-butoxide (1.46 g, 13 mmol) and DMSO (20 mL) was stirred under nitrogen at 85° C. After the reaction was completed, the mixture was poured into water (200 mL). The precipitate was filtered, washed with water and dried to give RM1-01 (3.15 g), yield: 83%.

$^1$H-NMR for compound RM1-01 (400 MHz, d$^6$-DMSO): δ: 8.71-8.70 (d, J=5.0 Hz, 1H), 8.68 (s, 1H), 7.90 (brs, 1H), 7.77 (brs, 1H), 7.56 (s, 1H), 6.73-6.69 (m, 1H), 6.64-6.68 (d, J=5.0 Hz, 1H), 6.16 (s, sH), 4.05 (s, 3H).

$^{13}$C-NMR for the compound RM1-01 (100 MHz, d$^6$-DMSO): δ: 165.62 (s), 160.75 (s), 158.12 (s), 155.01 (s), 153.40 (m), 152.90 (m), 151.47 (s), 144.76 (m), 125.61 (s), 124.12 (m), 118.49 (s), 113.45 (s), 109.97 (s), 101.40 (s), 100.32 (m), 97.19 (m), 56.35 (s).

$^{19}$F-NMR for the compound RM1-01 (377 MHz, d$^6$-DMSO): δ: −128.84 (s), −130.11 (s).

ESI-MS [(M+H)$^+$]: m/z calculated: 380.1, founded: 380.3.

1.2 Synthesis of Compound RM2-01

To a mixture of RM1-01 (3.80 g, 10 mmol), DMF (20 mL) and pyridine (40 mmol) in a 50 mL flask, phenyl chloroformate (30 mmol) was added dropwise below 10° C. After the reaction was completed, the mixture was dropped into water (100 mL). The precipitate was filtered and purified by column chromatography to obtain RM2-01 (3.36 g), yield: 67%.

$^1$H-NMR for the compound RM2-01 (400 MHz, DMSO) δ: 10.29 (s, 1H), 8.73 (d, 1H), 8.67 (s, 1H), 7.89-7.84 (m, 2H), 7.77 (s, 1H), 7.58 (s, 1H), 7.48 (t, 2H), 7.31 (m, 3H), 6.86 (d, 1H), 4.05 (s, 3H). $^{19}$F-NMR for the compound RM2-01 (377 MHz, DMSO) δ: −125.77 (s), 127.84 (s).

1.3 Synthesis of Compound III-01

A mixture of RM2-01 (500 mg, 1 mmol), acetonitrile (10 mL) and SM3-01 (30 mmol) was stirred at 60° C. After the reaction was completed, the precipitate was filtered, dried and purified by column chromatography to give III-01 (302 mg), yield: 65%.

$^1$H-NMR for the compound III-01 (400 MHz, DMSO) δ: 8.73-8.72 (d, J=5.2 Hz, 1H), 8.70 (s, 1H), 8.36 (s, 1H), 8.33-8.29 (dd, 1H), 7.93 (s, 1H), 7.81 (s, 1H), 7.58 (s, 1H), 7.44 (d, 1H), 6.77-6.76 (d, 1H), 4.07 (s, 3H), 2.62 (m, 1H), 0.71 (m, 2H), 0.47 (m, 2H).

$^{13}$C-NMR for the compound III-01 (100 MHz, DMSO) δ: 166.30 (s), 160.64 (s), 158.66 (s), 155.56 (s), 154.84/152.40 (m), 153.84 (s), 152.93/150.49 (m), 151.99 (s), 136.82/136.70 (m), 126.29 (s), 124.52 (s), 123.62/123.45/123.27 (m), 113.81 (s), 108.48 (s), 105.65/105.43 (m), 103.20/102.94 (m), 102.12 (s), 56.71 (s), 22.80 (s), 6.66/6.54 (d).

$^{19}$F-NMR for the compound III-01 (377 MHz, DMSO) δ: −127.10 (s), −127.82 (s).

ESI-MS [(M+H)$^+$]: m/z calculated: 463.1, founded: 463.3.

Method 2 for Synthesis of Compound III-01

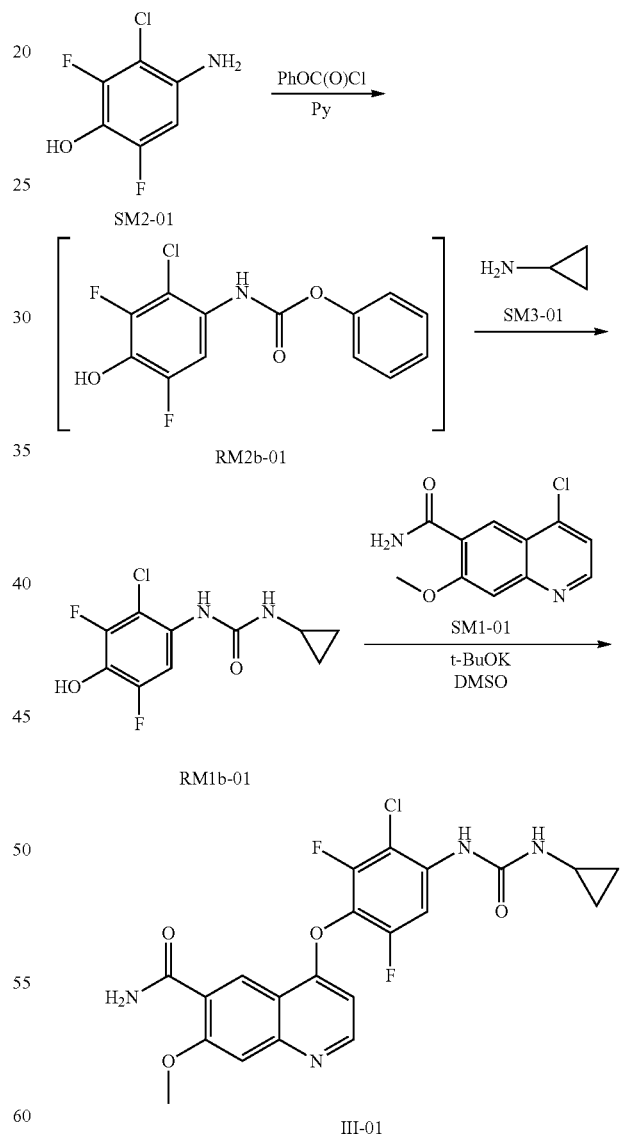

2.1 Synthesis of Intermediate RM1b-01

2.1-1: A mixture of SM2-01 (100 g, 0.56 mol), pyridine (58 g, 0.73 mol) and DMF (1 L) was stirred in the ice bath.

Phenyl chloroformate (96 g, 0.61 mol) was added dropwise below 10° C. After the reaction was completed, the reaction was to the next step directly.

$^1$H-NMR for RM2b-01, (DMSO, 400 MHz) δ: 10.71 (s, 1H), 9.78 (s, 1H), 7.44-7.36 (m, 3H), 7.27-7.19 (m, 3H).

$^{19}$F-NMR Spectrum (DMSO, 377 MHz) δ: −131.38/−131.42 (d), −132.79/−132.81 (d).

2.1-2: Cyclopropylamine (127 g, 2.24 mol) was added dropwise to step 2.1-1 reaction mixture below 10° C. Then the mixture was stirred at room temperature until the reaction was completed (IPC by HPLC). Acetonitrile (2 L) was added to the mixture, and the appeared precipitate was filtered. 6N—HCl was added dropwise to a mixture of the precipitate (143 g) and MeOH (600 mL). The mixture was stirred until fully soluble, and then water (3 L) was added. Then the appeared precipitate was filtered, washed with water (1 L) and dried to give RM1b-01 (117 g), yield: 80%.

$^1$H-NMR for RM1b-01 (400 MHz, DMSO) δ: 10.13 (s, 1H), 7.90 (s, 1H), 7.86-7.82 (dd, 1H), 7.11 (d, 1H), 2.56 (m, 1H), 0.67-0.62 (m, 2H), 0.43-0.39 (m, 2H);

$^{13}$C-NMR for RM1b-01 (100 MHz, DMSO) δ: 155.47 (s), 151.82 (m), 149.74 (m), 129.04 (m), 128.87-128.67 (m), 105.54 (m), 103.54 (m), 22.27 (s), 6.19 (s);

$^{19}$F-NMR for RM1b-01 (377 MHz, DMSO) δ: −132.09 (m).

ESI-MS [(M+H)+]: m/z calculated: 263.0, founded: 263.1.

2.2 Synthesis of Target Product III-01

A mixture of SM1-01 (20 g, 84 mmol), RM1b-01 (29 g, 110 mmol), potassium t-butoxide (12 g, 110 mmol) and DMSO (200 mL) was stirred at 65°. After the reaction was completed, the mixture was dropped into water (2 L). The appeared precipitate was filtered, washed with water and dried to give III-01 (24 g), yield: 73%.

NMR and LC-MS analyses were confirmed that the target compound III-01 could be reliably synthesized by the above two methods.

Example 3

Synthesis of Compound III-02

The synthesis of compound III-02 was carried out according to the method shown in example 2, in which compound SM3-02 (3 mmol) reacted with RM2-01 (1 mmol) in step 3. After the same post-treatment and drying, III-02 (354 mg, yield: 74%) was obtained.

ESI-MS [(M+H)$^+$]: m/z calculated: 479.1, founded: 479.3.

Example 4

Synthesis of Compound III-03

The synthesis of compound III-03 was carried out according to the method shown in example 2, in which compound SM3-03 (3 mmol) reacted with RM2-01 (1 mmol) in step 3. After the same post-treatment and drying, III-03 (297 mg, yield: 62%) was obtained.

ESI-MS [(M+H)$^+$]: m/z calculated: 479.1, founded: 479.3.

Example 5

Synthesis of Compound III-04

The synthesis of compound III-04 was carried out according to the method shown in example 2, in which compound SM3-04 (3 mmol) reacted with RM2-01 (1 mmol) in step 3. After the same post-treatment and drying, III-04 (316 mg, yield: 66%) was obtained.

ESI-MS [(M+H)$^+$]: m/z calculated: 479.1, founded: 479.3.

Example 6

Synthesis of Compound III-05

The synthesis of compound III-05 was carried out according to the method shown in example 2, in which compound SM3-05 (3 mmol) reacted with RM2-01 (1 mmol) in step 3. After the same post-treatment and drying, III-05 (229 mg, yield: 47%) was obtained.

ESI-MS [(M+H)$^+$]: m/z calculated: 487.1, founded: 487.3.

Example 7

Synthesis of Compound III-06

The synthesis of compound III-06 was carried out according to the method shown in example 2, in which compound SM3-06 (3 mmol) reacted with RM2-01 (1 mmol) in step 3. After the same post-treatment and drying, III-06 (271 mg, yield: 58%) was obtained.

ESI-MS [(M+H)$^+$]: m/z calculated: 467.1, founded: 467.3.

Example 8

Synthesis of Compound III-07

The synthesis of compound III-07 was carried out according to the method shown in example 2, in which compound SM3-07 (3 mmol) reacted with RM2-01 (1 mmol) in step 3. After the same post-treatment and drying, III-07 (293 mg, yield: 61%) was obtained.

ESI-MS [(M+H)$^+$]: m/z calculated: 481.1, founded: 481.3.

Example 9

Synthesis of Compound III-08

The synthesis of compound III-08 was carried out according to the method shown in example 2, in which compound SM3-08 (3 mmol) reacted with RM2-01 (1 mmol) in step 3. After the same post-treatment and drying, III-08 (317 mg, yield: 66%) was obtained.

ESI-MS [(M+H)$^+$]: m/z calculated: 481.1, founded: 481.3.

Example 10

Synthesis of Compound III-09

The synthesis of compound III-09 was carried out according to the method shown in example 2, in which compound SM3-09 (3 mmol) reacted with RM2-01 (1 mmol) in step 3. After the same post-treatment and drying, III-09 (327 mg, yield: 68%) was obtained.

ESI-MS [(M+H)$^+$]: m/z calculated: 481.1, founded: 481.3.

Example 11

Synthesis of Compound III-10

The synthesis of compound III-10 was carried out according to the method shown in example 2, in which compound SM3-10 (3 mmol) reacted with RM2-01 (1 mmol) in step 3. After the same post-treatment and drying, III-10 (303 mg, yield: 63%) was obtained.

ESI-MS [(M+H)$^+$]: m/z calculated: 481.1, founded: 481.3.

Example 12

Synthesis of Compound III-11

The synthesis of compound III-11 was carried out according to the method shown in example 2, in which compound SM3-11 (3 mmol) reacted with RM2-01 (1 mmol) in step 3. After the same post-treatment and drying, III-11 (302 mg, yield: 61%) was obtained.

ESI-MS [(M+H)$^+$]: m/z calculated: 495.1, founded: 495.0.

Example 13

Synthesis of Compound III-12

The synthesis of compound III-12 was carried out according to the method shown in example 2, in which compound SM3-12 (3 mmol) reacted with RM2-01 (1 mmol) in step 3. After the same post-treatment and drying, III-12 (297 mg, yield: 60%) was obtained.

ESI-MS [(M+H)$^+$]: m/z calculated: 495.1, founded: 495.3.

Example 14

Synthesis of Compound III-13

The synthesis of compound III-13 was carried out according to the method shown in example 2, in which compound SM3-13 (3 mmol) reacted with RM2-01 (1 mmol) in step 3. After the same post-treatment and drying, III-13 (343 mg, yield: 69%) was obtained.

ESI-MS [(M+H)$^+$]: m/z calculated: 497.1, founded: 497.3.

Example 15

Synthesis of Compound III-14

The synthesis of compound III-14 was carried out according to the method shown in example 2, in which compound SM3-14 (3 mmol) reacted with RM2-01 (1 mmol) in step 3. After the same post-treatment and drying, III-14 (283 mg, yield: 58%) was obtained.

ESI-MS [(M+H)$^+$]: m/z calculated: 497.1, founded: 497.3.

Example 16

Synthesis of Compound III-15

The synthesis of compound III-15 was carried out according to the method shown in example 2, in which compound SM345 (3 mmol) reacted with RM2-01 (1 mmol) in step 3. After the same post-treatment and drying, III-15 (293 mg, yield: 59%) was obtained.

ESI-MS [(M+H)$^+$]: m/z calculated: 497.1, founded: 497.3.

Example 17

Synthesis of Compound III-16

Step 1: A mixture of SM1-01 (2.36 g, 10 mmol), SM2-02 (2.12 g, 13 mmol), potassium t-butoxide (1.46 g, 13 mmol) and DMSO (20 mL) was stirred under nitrogen at 85° C. After the reaction was completed, the mixture was poured into water (200 mL). The precipitate was filtered, washed with water and dried to give RM1-02 (2.98 g), yield: 82%.

Step 2: To a mixture of RM1-02 (3.63 g, 10 mmol), DMF (20 mL) and pyridine (40 mmol) in a 50 mL flask, phenyl chloroformate (30 mmol) was added dropwise below 10° C. After the reaction was completed, the mixture was dropped into water (100 mL). The precipitate was filtered and purified by column chromatography to obtain RM2-02 (3.43 g), yield: 71%.

Step 3: A mixture of RM2-02 (483 mg, 1 mmol), acetonitrile (10 mL) and SM3-01 (30 mmol) was stirred at 60° C. After the reaction was completed, the precipitate was filtered and dried to obtain III-16 (330 mg), yield: 74%.

$^1$H-NMR for the compound III-16 (400 MHz, d$_6$-DMSO) δ: 8.72-8.71 (m, 2H), 8.67 (s, 1H), 8.20-8.16 (m, 1H), 7.91 (s, 1H), 7.80 (s, 1H), 7.60 (s, 1H), 6.96 (d, 1H), 6.78-6.77 (d, J=5.0 Hz, 1H), 4.05 (s, 3H), 2.61 (m, 1H), 0.70 (m, 2H), 0.46 (m, 2H).

$^{19}$F-NMR for the compound III-16 (377 MHz, d$_6$-DMSO) δ: −132.37 (d, 1F), −151.18 (d, 1F), −156.64 (s, 1F).

ESI-MS [(M+H)$^+$]: m/z calculated: 447.1, founded: 447.3.

Example 18

Synthesis of Compound III-17

Step 1: A mixture of SM1-01 (2.36 g, 10 mmol), SM2-03 (2.91 g, 13 mmol), potassium t-butoxide (1.46 g, 13 mmol) and DMSO (20 mL) was stirred under nitrogen at 85° C. After the reaction was completed, the mixture was poured into water (200 mL). The precipitate was filtered, washed with water and dried to give RM1-03 (2.93 g), yield: 69%.

Step 2: To a mixture of RM1-03 (4.24 g, 10 mmol), DMF (20 mL) and pyridine (40 mmol) in a 50 mL flask, phenyl chloroformate (30 mmol) was added dropwise below 10° C. After the reaction was completed, the mixture was dropped into water (100 mL). The precipitate was filtered and purified by column chromatography to obtain RM2-03 (3.10 g), yield: 57%.

Step 3: A mixture of RM2-02 (544 mg, 1 mmol), acetonitrile (10 mL) and SM3-01 (30 mmol) was stirred at 60° C. After the reaction was completed, the precipitate was filtered and dried to obtain III-17 (278 mg), yield: 55%.

ESI-MS [(M+H)$^+$]: m/z calculated: 507.0, founded: 507.2.

Example 19

Synthesis of Compound III-18

Step 1: A mixture of SM1-01 (2.36 g, 10 mmol), SM2-07 (3.13 g, 13 mmol), potassium t-butoxide (1.46 g, 13 mmol)

and DMSO (20 mL) was stirred under nitrogen at 85° C. After the reaction was completed, the mixture was poured into water (200 mL). The precipitate was filtered, washed with water and dried to give RM1-07 (1.85 g), yield: 42%.

Step 2: To a mixture of RM1-07 (4.41 g, 10 mmol), DMF (20 mL) and pyridine (40 mmol) in a 50 mL flask, phenyl chloroformate (30 mmol) was added dropwise below 10° C. After the reaction was completed, the mixture was dropped into water (100 mL). The precipitate was filtered and purified by column chromatography to obtain RM2-07 (2.69 g), yield: 48%.

Step 3: A mixture of RM2-07 (561 mg, 1 mmol), acetonitrile (10 mL) and SM3-01 (30 mmol) was stirred at 60° C. After the reaction was completed, the precipitate was filtered and dried to obtain III-18 (330 mg), yield: 63%.

ESI-MS [(M+H)$^+$]: m/z calculated: 523.0, founded: 523.0.

Example 20

Synthesis of Compound III-19

Step 1: A mixture of SM1-01 (2.36 g, 10 mmol), SM2-04 (2.55 g, 13 mmol), potassium t-butoxide (1.46 g, 13 mmol) and DMSO (20 mL) was stirred under nitrogen at 85° C. After the reaction was completed, the mixture was poured into water (200 mL). The precipitate was filtered, washed with water and dried to give RM1-04 (2.93 g), yield: 74%.

Step 2: To a mixture of RM1-04 (3.96 g, 10 mmol), DMF (20 mL) and pyridine (40 mmol) in a 50 mL flask, phenyl chloroformate (30 mmol) was added dropwise below 10° C. After the reaction was completed, the mixture was dropped into water (100 mL). The precipitate was filtered and purified by column chromatography to obtain RM2-04 (3.10 g), yield: 57%.

Step 3: A mixture of RM2-07 (516 mg, 1 mmol), acetonitrile (10 mL) and SM3-01 (30 mmol) was stirred at 60° C. After the reaction was completed, the precipitate was filtered and dried to obtain III-19 (153 mg), yield: 32%.

ESI-MS [(M+H)$^+$]: m/z calculated: 479.1, founded: 479.3.

Example 21

Synthesis of Compound III-20

Step 1: A mixture of SM1-01 (2.36 g, 10 mmol), SM2-05 (3.13 g, 13 mmol), potassium t-butoxide (1.46 g, 13 mmol) and DMSO (20 mL) was stirred under nitrogen at 85° C. After the reaction was completed, the mixture was poured into water (200 mL). The precipitate was filtered, washed with water and dried to give RM1-05 (2.93 g), yield: 66%.

Step 2: To a mixture of RM1-05 (4.41 g, 10 mmol), DMF (20 mL) and pyridine (40 mmol) in a 50 mL flask, phenyl chloroformate (30 mmol) was added dropwise below 10° C. After the reaction was completed, the mixture was dropped into water (100 mL). The precipitate was filtered and purified by column chromatography to obtain RM2-05 (3.10 g), yield: 55%.

Step 3: A mixture of RM2-05 (561 mg, 1 mmol), acetonitrile (10 mL) and SM3-01 (30 mmol) was stirred at 60° C. After the reaction was completed, the precipitate was filtered and dried to obtain III-20 (136 mg), yield: 26%.

ESI-MS [(M+H)$^+$]: m/z calculated: 522.0, founded: 522.2.

Example 22

Synthesis of Compound III-21

The synthesis of compound III-21 was carried out according to the method shown in example 16, in which compound SM3-17 (3 mmol) reacted with RM2-02 (1 mmol) in step 3. After the same post-treatment and drying, III-21 (327 mg, yield: 71%) was obtained.

ESI-MS [(M+H)$^+$]: m/z calculated: 461.1, founded: 461.3.

Example 23

Synthesis of Compound III-22

The synthesis of compound III-22 was carried out according to the method shown in example 2, in which compound SM3-17 (3 mmol) reacted with RM2-01 (1 mmol) in step 3. After the same post-treatment and drying, III-22 (353 mg, yield: 74%) was obtained.

ESI-MS [(M+H)$^+$]: m/z calculated: 477.1, founded: 477.3.

Example 24

Synthesis of Compound III-23

The synthesis of compound III-23 was carried out according to the method shown in example 16, in which compound SM3-18 (3 mmol) reacted with RM2-02 (1 mmol) in step 3. After the same post-treatment and drying, III-23 (197 mg, yield: 41%) was obtained.

ESI-MS [(M+H)$^+$]: m/z calculated: 483.1, founded: 483.4.

Example 25

Synthesis of Compound III-24

The synthesis of compound III-24 was carried out according to the method shown in example 2, in which compound SM3-18 (3 mmol) reacted with RM2-01 (1 mmol) in step 3. After the same post-treatment and drying, III-24 (236 mg, yield: 47%) was obtained.

ESI-MS [(M+H)$^+$]: m/z calculated: 499.1, founded: 499.3.

Example 26

Synthesis of Compound III-25

The synthesis of compound III-25 was carried out according to the method shown in example 2, in which compound SM3-19 (3 mmol) reacted with RM2-01 (1 mmol) in step 3. After the same post-treatment and drying, III-25 (301 mg, yield: 63%) was obtained.

ESI-MS [(M+H)$^+$]: m/z calculated: 477.1, founded: 477.3.

Example 27

Synthesis of Compound III-26

The synthesis of compound III-26 was carried out according to the method shown in example 2, in which compound SM3-20 (3 mmol) reacted with RM2-01 (1 mmol) in step 3. After the same post-treatment and drying, III-26 (277 mg, yield: 58%) was obtained.

ESI-MS [(M+H)$^+$]: m/z calculated: 477.1, founded: 477.3.

Example 28

Synthesis of Compound III-27

The synthesis of compound III-27 was carried out according to the method shown in example 2, in which compound SM3-21 (3 mmol) reacted with RM2-01 (1 mmol) in step 3. After the same post-treatment and drying, III-27 (369 mg, yield: 77%) was obtained.

ESI-MS [(M+H)$^+$]: m/z calculated: 479.1, founded: 479.3.

Example 29

Synthesis of Compound III-28

The synthesis of compound III-28 was carried out according to the method shown in example 16, in which compound SM3-22 (3 mmol) reacted with RM2-01 (1 mmol) in step 3. After the same post-treatment and drying, III-28 (324 mg, yield: 64%) was obtained.

ESI-MS [(M+H)$^+$]: m/z calculated: 507.1, founded: 507.3.

Example 30

Synthesis of Compound III-29

The synthesis of compound III-29 was carried out according to the method shown in example 2, in which compound SM3-23 (3 mmol) reacted with RM2-01 (1 mmol) in step 3. After the same post-treatment and drying, III-29 (261 mg, yield: 53%) was obtained.

ESI-MS [(M+H)$^+$]: m/z calculated: 493.1, founded: 493.3.

Example 31

Synthesis of Compound III-30

The synthesis of compound III-30 was carried out according to the method shown in example 2, in which compound SM3-24 (3 mmol) reacted with RM2-01 (1 mmol) in step 3. After the same post-treatment and drying, III-30 (237 mg, yield: 48%) was obtained.

ESI-MS [(M+H)$^+$]: m/z calculated: 493.1, founded: 493.2.

Example 32

Synthesis of Compound III-31

The synthesis of compound III-31 was carried out according to the method shown in example 2, in which compound SM3-25 (3 mmol) reacted with RM2-01 (1 mmol) in step 3. After the same post-treatment and drying, III-31 (271 mg, yield: 55%) was obtained.

ESI-MS [(M+H)$^+$]: m/z calculated: 493.1, founded: 493.1.

Example 33

Synthesis of Compound III-32

The synthesis of compound III-32 was carried out according to the method shown in example 2, in which compound SM3-26 (3 mmol) reacted with RM2-01 (1 mmol) in step 3. After the same post-treatment and drying, III-32 (232 mg, yield: 47%) was obtained.

ESI-MS [(M+H)$^+$]: m/z calculated: 493.1, founded: 493.1.

Example 34

Synthesis of Compound III-33

The synthesis of compound III-33 was carried out according to the method shown in example 2, in which compound SM3-27 (3 mmol) reacted with RM2-01 (1 mmol) in step 3. After the same post-treatment and drying, III-33 (324 mg, yield: 64%) was obtained.

ESI-MS [(M+H)$^+$]: m/z calculated: 506.1, founded: 506.1.

Example 35

Synthesis of Compound III-34

The synthesis of compound III-34 was carried out according to the method shown in example 2, in which compound SM3-16 (3 mmol) reacted with RM2-01 (1 mmol) in step 3. After the same post-treatment and drying, III-34 (384 mg, yield: 83%) was obtained.

$^1$H-NMR for the compound III-34 (400 MHz, DMSO) δ: 8.71-8.70 (d, 1H), 8.65 (s, 1H), 8.38 (s, 1H), 8.33-8.29 (dd, 1H), 7.91 (s, 1H), 7.79 (s, 1H), 7.56 (s, 1H), 7.21-7.20 (d, 1H), 6.76-6.75 (d, 1H), 4.04 (s, 3H), 3.78 (m, 1H), 1.41-1.23 (d, 6H).

ESI-MS [(M+H)$^+$]: m/z calculated: 465.1, founded: 465.3.

Example 36

Synthesis of Compound III-35

Step 1: A mixture of SM1-01 (2.36 g, 10 mmol), SM2-08 (2.33 g, 13 mmol), potassium t-butoxide (1.46 g, 13 mmol) and DMSO (20 mL) was stirred under nitrogen at 85° C. After the reaction was completed, the mixture was poured into water (200 mL). The precipitate was filtered, washed with water and dried to give RM1-08 (3.15 g), yield: 83%.

Step 2: To a mixture of RM1-08 (3.80 g, 10 mmol), DMF (20 mL) and pyridine (40 mmol) in a 50 mL flask, phenyl chloroformate (30 mmol) was added dropwise below 10° C. After the reaction was completed, the mixture was dropped into water (100 mL). The precipitate was filtered and purified by column chromatography to obtain RM2-08 (3.35 g), yield: 67%.

Step 3: A mixture of RM2-08 (500 mg, 1 mmol), acetonitrile (10 mL) and SM3-01 (30 mmol) was stirred at 60° C. After the reaction was completed, the precipitate was filtered and dried to obtain III-35 (301 mg), yield: 65%.

ESI-MS [(M+H)$^+$]: m/z calculated: 463.1, founded: 462.9.

Example 37

Synthesis of Compound III-36

Step 1: A mixture of SM1-01 (2.36 g, 10 mmol), SM2-09 (2.35 g, 13 mmol), potassium t-butoxide (1.46 g, 13 mmol) and DMSO (20 mL) was stirred under nitrogen at 85° C. After the reaction was completed, the mixture was poured into water (200 mL). The precipitate was filtered, washed with water and dried to give RM1-09 (2.32 g), yield: 61%.

Step 2: To a mixture of RM1-09 (3.81 g, 10 mmol), DMF (20 mL) and pyridine (40 mmol) in a 50 mL flask, phenyl chloroformate (30 mmol) was added dropwise below 10° C. After the reaction was completed, the mixture was dropped into water (100 mL). The precipitate was filtered and purified by column chromatography to obtain RM2-09 (2.60 g), yield: 52%.

Step 3: A mixture of RM2-09 (501 mg, 1 mmol), acetonitrile (10 mL) and SM3-01 (30 mmol) was stirred at 60° C. After the reaction was completed, the precipitate was filtered and dried to obtain III-36 (274 mg), yield: 59%.

ESI-MS [(M+H)$^+$]: m/z calculated: 465.1, founded: 465.0.

Example 38

Synthesis of Compound III-37

The synthesis of compound III-37 was carried out according to the method shown in example 2, in which compound SM3-29 (3 mmol) reacted with RM2-01 (1 mmol) in step 3. After the same post-treatment and drying, III-37 (263 mg, yield: 46%) was obtained.

ESI-MS [(M+H)$^+$]: m/z calculated: 572.1, founded: 572.0.

Example 39

Synthesis of Compound III-38

The synthesis of compound III-38 was carried out according to the method shown in example 2, in which compound SM3-30 (3 mmol) reacted with RM2-01 (1 mmol) in step 3. After the same post-treatment and drying, III-38 (296 mg, yield: 57%) was obtained.

ESI-MS [(M+H)$^+$]: m/z calculated: 519.1, founded: 518.9.

Example 40

Synthesis of Compound III-39

The synthesis of compound III-39 was carried out according to the method shown in example 2, in which compound SM3-31 (3 mmol) reacted with RM2-01 (1 mmol) in step 3. After the same post-treatment and drying, III-39 (180 mg, yield: 34%) was obtained.

ESI-MS [(M+H)$^+$]: m/z calculated: 531.1, founded: 530.9.

Example 41

Synthesis of Compound III-40

Step 1: A mixture of SM1-01 (2.36 g, 10 mmol), SM2-10 (2.28 g, 13 mmol), potassium t-butoxide (1.46 g, 13 mmol) and DMSO (20 mL) was stirred under nitrogen at 85° C. After the reaction was completed, the mixture was poured into water (200 mL). The precipitate was filtered, washed with water and dried to give RM1-10 (2.85 g), yield: 76%.

Step 2: To a mixture of RM1-10 (3.75 g, 10 mmol), DMF (20 mL) and pyridine (40 mmol) in a 50 mL flask, phenyl chloroformate (30 mmol) was added dropwise below 10° C. After the reaction was completed, the mixture was dropped into water (100 mL). The precipitate was filtered and purified by column chromatography to obtain RM2-10 (3.37 g), yield: 68%.

Step 3: A mixture of RM2-10 (495 mg, 1 mmol), acetonitrile (10 mL) and SM3-01 (30 mmol) was stirred at 60° C. After the reaction was completed, the precipitate was filtered and dried to obtain III-40 (289 mg), yield: 63%.

ESI-MS [(M+H)$^+$]: m/z calculated: 459.1, founded: 459.0.

Example 42

Synthesis of Compound III-41

Step 1: A mixture of SM1-01 (2.36 g, 10 mmol), SM2-11 (2.49 g, 13 mmol), potassium t-butoxide (1.46 g, 13 mmol) and DMSO (20 mL) was stirred under nitrogen at 85° C. After the reaction was completed, the mixture was poured into water (200 mL). The precipitate was filtered, washed with water and dried to give RM1-11 (2.31 g), yield: 59%.

Step 2: To a mixture of RM1-11 (3.92 g, 10 mmol), DMF (20 mL) and pyridine (40 mmol) in a 50 mL flask, phenyl chloroformate (30 mmol) was added dropwise below 10° C. After the reaction was completed, the mixture was dropped into water (100 mL). The precipitate was filtered and purified by column chromatography to obtain RM2-11 (3.28 g), yield: 64%.

Step 3: A mixture of RM2-11 (512 mg, 1 mmol), acetonitrile (10 mL) and SM3-01 (30 mmol) was stirred at 60° C. After the reaction was completed, the precipitate was filtered and dried to obtain III-41 (334 mg), yield: 70%.

ESI-MS [(M+H)$^+$]: m/z calculated: 475.1, founded: 475.0.

Example 43

Synthesis of Compound III-42

Step 1: A mixture of SM1-01 (2.36 g, 10 mmol), SM2-12 (2.53 g, 13 mmol), potassium t-butoxide (1.46 g, 13 mmol) and DMSO (20 mL) was stirred under nitrogen at 85° C. After the reaction was completed, the mixture was poured into water (200 mL). The precipitate was filtered, washed with water and dried to give RM1-12 (2.53 g), yield: 64%.

Step 2: To a mixture of RM1-12 (3.95 g, 10 mmol), DMF (20 mL) and pyridine (40 mmol) in a 50 mL flask, phenyl chloroformate (30 mmol) was added dropwise below 10° C. After the reaction was completed, the mixture was dropped into water (100 mL). The precipitate was filtered and purified by column chromatography to obtain RM2-12 (3.45 g), yield: 67%.

Step 3: A mixture of RM2-12 (515 mg, 1 mmol), acetonitrile (10 mL) and SM3-01 (30 mmol) was stirred at 60° C. After the reaction was completed, the precipitate was filtered and dried to obtain III-42 (296 mg), yield: 62%.

ESI-MS [(M+H)$^+$]: m/z calculated: 478.1, founded: 478.0.

Example 44

Synthesis of Compound III-43

Step 1: A mixture of SM1-01 (2.36 g, 10 mmol), SM2-13 (2.85 g, 13 mmol), potassium t-butoxide (1.46 g, 13 mmol) and DMSO (20 mL) was stirred under nitrogen at 85° C. After the reaction was completed, the mixture was poured into water (200 mL). The precipitate was filtered, washed with water and dried to give RM1-13 (2.98 g), yield: 71%.

Step 2: To a mixture of RM1-13 (4.20 g, 10 mmol), DMF (20 mL) and pyridine (40 mmol) in a 50 mL flask, phenyl chloroformate (30 mmol) was added dropwise below 10° C. After the reaction was completed, the mixture was dropped into water (100 mL). The precipitate was filtered and purified by column chromatography to obtain RM2-13 (3.08 g), yield: 57%.

Step 3: A mixture of RM2-13 (540 mg, 1 mmol), acetonitrile (10 mL) and SM3-01 (30 mmol) was stirred at 60° C. After the reaction was completed, the precipitate was filtered and dried to obtain III-43 (196 mg), yield: 39%.

ESI-MS [(M+H)$^+$]: m/z calculated: 503.1, founded: 503.0.

Example 45

Synthesis of Compound III-44

Step 1: A mixture of SM1-01 (2.36 g, 10 mmol), SM2-14 (2.83 g, 13 mmol), potassium t-butoxide (1.46 g, 13 mmol) and DMSO (20 mL) was stirred under nitrogen at 85° C. After the reaction was completed, the mixture was poured into water (200 mL). The precipitate was filtered, washed with water and dried to give RM1-14 (2.72 g), yield: 65%.

Step 2: To a mixture of RM1-14 (4.18 g, 10 mmol), DMF (20 mL) and pyridine (40 mmol) in a 50 mL flask, phenyl chloroformate (30 mmol) was added dropwise below 10° C. After the reaction was completed, the mixture was dropped into water (100 mL). The precipitate was filtered and purified by column chromatography to obtain RM2-14 (3.28 g), yield: 61%.

Step 3: A mixture of RM2-14 (538 mg, 1 mmol), acetonitrile (10 mL) and SM3-01 (30 mmol) was stirred at 60° C. After the reaction was completed, the precipitate was filtered and dried to obtain III-44 (190 mg), yield: 38%.

ESI-MS [(M+H)$^+$]: m/z calculated: 501.1, founded: 501.0.

Example 46

Synthesis of Compound III-45

Step 1: A mixture of SM1-01 (2.36 g, 10 mmol), SM245 (3.14 g, 13 mmol), potassium t-butoxide (1.46 g, 13 mmol) and DMSO (20 mL) was stirred under nitrogen at 85° C. After the reaction was completed, the mixture was poured into water (200 mL). The precipitate was filtered, washed with water and dried to give RM1-15 (2.70 g), yield: 61%.

Step 2: To a mixture of RM1-15 (4.42 g, 10 mmol), DMF (20 mL) and pyridine (40 mmol) in a 50 mL flask, phenyl chloroformate (30 mmol) was added dropwise below 10° C. After the reaction was completed, the mixture was dropped into water (100 mL). The precipitate was filtered and purified by column chromatography to obtain RM245 (3.99 g), yield: 71%.

Step 3: A mixture of RM245 (563 mg, 1 mmol), acetonitrile (10 mL) and SM3-01 (30 mmol) was stirred at 60° C. After the reaction was completed, the precipitate was filtered and dried to obtain III-45 (221 mg), yield: 42%.

ESI-MS [(M+H)$^+$]: m/z calculated: 525.1, founded: 525.0.

Example 47

Synthesis of Compound III-46

Step 1: A mixture of SM1-01 (2.36 g, 10 mmol), SM2-16 (3.37 g, 13 mmol), potassium t-butoxide (1.46 g, 13 mmol) and DMSO (20 mL) was stirred under nitrogen at 85° C. After the reaction was completed, the mixture was poured into water (200 mL). The precipitate was filtered, washed with water and dried to give RM1-16 (2.81 g), yield: 61%.

Step 2: To a mixture of RM1-16 (4.60 g, 10 mmol), DMF (20 mL) and pyridine (40 mmol) in a 50 mL flask, phenyl chloroformate (30 mmol) was added dropwise below 10° C. After the reaction was completed, the mixture was dropped into water (100 mL). The precipitate was filtered and purified by column chromatography to obtain RM2-16 (2.84 g), yield: 49%.

Step 3: A mixture of RM2-16 (580 mg, 1 mmol), acetonitrile (10 mL) and SM3-01 (30 mmol) was stirred at 60° C. After the reaction was completed, the precipitate was filtered and dried to obtain III-46 (196 mg), yield: 36%.

ESI-MS [(M+H)$^+$]: m/z calculated: 543.1, founded: 543.0.

Example 48

Synthesis of Compound III-47

Step 1: A mixture of SM1-01 (2.36 g, 10 mmol), SM2-17 (2.65 g, 13 mmol), potassium t-butoxide (1.46 g, 13 mmol) and DMSO (20 mL) was stirred under nitrogen at 85° C. After the reaction was completed, the mixture was poured into water (200 mL). The precipitate was filtered, washed with water and dried to give RM1-17 (2.68 g), yield: 69%.

Step 2: To a mixture of RM1-17 (3.88 g, 10 mmol), DMF (20 mL) and pyridine (40 mmol) in a 50 mL flask, phenyl chloroformate (30 mmol) was added dropwise below 10° C. After the reaction was completed, the mixture was dropped into water (100 mL). The precipitate was filtered and purified by column chromatography to obtain RM2-17 (3.36 g), yield: 66%.

Step 3: A mixture of RM2-17 (509 mg, 1 mmol), acetonitrile (10 mL) and SM3-01 (30 mmol) was stirred at 60° C. After the reaction was completed, the precipitate was filtered and dried to obtain III-47 (236 mg), yield: 50%.

ESI-MS [(M+H)$^+$]: m/z calculated: 472.2, founded: 472.0.

Example 49

Synthesis of Compound III-48

Step 1: A mixture of SM1-01 (2.36 g, 10 mmol), SM2-18 (2.87 g, 13 mmol), potassium t-butoxide (1.46 g, 13 mmol) and DMSO (20 mL) was stirred under nitrogen at 85° C. After the reaction was completed, the mixture was poured into water (200 mL). The precipitate was filtered, washed with water and dried to give RM1-18 (2.59 g), yield: 64%.

Step 2: To a mixture of RM1-18 (4.05 g, 10 mmol), DMF (20 mL) and pyridine (40 mmol) in a 50 mL flask, phenyl chloroformate (30 mmol) was added dropwise below 10° C. After the reaction was completed, the mixture was dropped into water (100 mL). The precipitate was filtered and purified by column chromatography to obtain RM2-18 (2.78 g), yield: 53%.

Step 3: A mixture of RM2-18 (525 mg, 1 mmol), acetonitrile (10 mL) and SM3-01 (30 mmol) was stirred at 60° C. After the reaction was completed, the precipitate was filtered and dried to obtain III-48 (205 mg), yield: 42%.

ESI-MS [(M+H)$^+$]: m/z calculated: 488.1, founded: 488.0.

Example 50

Synthesis of Compound III-49

Step 1: A mixture of SM1-01 (2.36 g, 10 mmol), SM2-19 (3.21 g, 13 mmol), potassium t-butoxide (1.46 g, 13 mmol) and DMSO (20 mL) was stirred under nitrogen at 85° C. After the reaction was completed, the mixture was poured into water (200 mL). The precipitate was filtered, washed with water and dried to give RM1-19 (2.67 g), yield: 62%.

Step 2: To a mixture of RM1-19 (4.31 g, 10 mmol), DMF (20 mL) and pyridine (40 mmol) in a 50 mL flask, phenyl chloroformate (30 mmol) was added dropwise below 10° C. After the reaction was completed, the mixture was dropped into water (100 mL). The precipitate was filtered and purified by column chromatography to obtain RM2-19 (2.70 g), yield: 49%.

Step 3: A mixture of RM2-19 (551 mg, 1 mmol), acetonitrile (10 mL) and SM3-01 (30 mmol) was stirred at 60° C. After the reaction was completed, the precipitate was filtered and dried to obtain III-49 (231 mg), yield: 45%.

ESI-MS [(M+H)$^+$]: m/z calculated: 514.2, founded: 514.0.

Example 51

Synthesis of Compound III-50

Step 1: A mixture of SM1-01 (2.36 g, 10 mmol), SM2-20 (2.51 g, 13 mmol), potassium t-butoxide (1.46 g, 13 mmol) and DMSO (20 mL) was stirred under nitrogen at 85° C. After the reaction was completed, the mixture was poured into water (200 mL). The precipitate was filtered, washed with water and dried to give RM1-20 (2.40 g), yield: 61%.

Step 2: To a mixture of RM1-20 (3.93 g, 10 mmol), DMF (20 mL) and pyridine (40 mmol) in a 50 mL flask, phenyl chloroformate (30 mmol) was added dropwise below 10° C. After the reaction was completed, the mixture was dropped into water (100 mL). The precipitate was filtered and purified by column chromatography to obtain RM2-20 (2.82 g), yield: 55%.

Step 3: A mixture of RM2-20 (513 mg, 1 mmol), acetonitrile (10 mL) and SM3-01 (30 mmol) was stirred at 60° C. After the reaction was completed, the precipitate was filtered and dried to obtain III-50 (186 mg), yield: 39%.

ESI-MS [(M+H)$^+$]: m/z calculated: 477.1, founded: 476.9.

Example 51

Synthesis of Compound III-51

Step 1: A mixture of SM1-01 (2.36 g, 10 mmol), SM2-21 (2.68 g, 13 mmol), potassium t-butoxide (1.46 g, 13 mmol) and DMSO (20 mL) was stirred under nitrogen at 85° C. After the reaction was completed, the mixture was poured into water (200 mL). The precipitate was filtered, washed with water and dried to give RM1-21 (2.31 g), yield: 57%.

Step 2: To a mixture of RM1-21 (4.06 g, 10 mmol), DMF (20 mL) and pyridine (40 mmol) in a 50 mL flask, phenyl chloroformate (30 mmol) was added dropwise below 10° C. After the reaction was completed, the mixture was dropped into water (100 mL). The precipitate was filtered and purified by column chromatography to obtain RM2-21 (2.37 g), yield: 45%.

Step 3: A mixture of RM2-21 (527 mg, 1 mmol), acetonitrile (10 mL) and SM3-01 (30 mmol) was stirred at 60° C. After the reaction was completed, the precipitate was filtered and dried to obtain III-51 (132 mg), yield: 27%.

ESI-MS [(M+H)$^+$]: m/z calculated: 490.2, founded: 490.0.

Example 53

Synthesis of Compound III-52

Step 1: A mixture of SM1-01 (2.36 g, 10 mmol), SM2-22 (3.01 g, 13 mmol), potassium t-butoxide (1.46 g, 13 mmol) and DMSO (20 mL) was stirred under nitrogen at 85° C. After the reaction was completed, the mixture was poured into water (200 mL). The precipitate was filtered, washed with water and dried to give RM1-22 (2.67 g), yield: 62%.

Step 2: To a mixture of RM1-22 (4.31 g, 10 mmol), DMF (20 mL) and pyridine (40 mmol) in a 50 mL flask, phenyl chloroformate (30 mmol) was added dropwise below 10° C. After the reaction was completed, the mixture was dropped into water (100 mL). The precipitate was filtered and purified by column chromatography to obtain RM2-22 (3.26 g), yield: 59%.

Step 3: A mixture of RM2-22 (552 mg, 1 mmol), acetonitrile (10 mL) and SM3-01 (30 mmol) was stirred at 60° C. After the reaction was completed, the precipitate was filtered and dried to obtain III-52 (175 mg), yield: 34%.

ESI-MS [(M+H)$^+$]: m/z calculated: 515.2, founded: 515.0.

Example 54

The Single Crystal Structure of III-01:

The single crystal of III-01 was obtained by solution generation method. A solution of III-01 (15 mg), DMSO (5 mg) and methyl tetrahydrofuran (3 mL) was heated to be clear. The filtrate was left to stand until the single crystal of III-01 was appeared and obtained. The crystal structure is shown as follows.

Example 55: The Pharmacodynamics Experiments of Tumor Inhibition In Vitro

The compound prepared by the present invention can be screened for its effect on target inhibition of several tumor cell lines including liver cancer cell line (Hep3B 2.1-7), bladder cancer cell line (RT112/84), thyroid cancer cell line (TT), cervical cancer cell line (Hela), and leukemia cell line (K562) by the following preclinical in vitro inhibition assays. And further to screen better new anti-cancer drugs by measuring the inhibitory activity of more than ten RTK targets such as VEGFR1-3, FGFR1-4, EGFR, c-MET, RET, PDGFRα, etc. The efficacy of the new drug is then finally confirmed by clinical trials. Other methods are also apparent to those with general skills in the field.

This embodiment investigates the proliferation inhibitory effect of compounds (III III-52) on tumor cells.

1. On the first day of the cell spreading experiment, 96-well cell culture plates (Corning 3917 plates) were evenly spread with 100 ul per well containing 5000 cells (e.g.: hepatocellular carcinoma cell line (Hep3B 2.1-7), bladder cancer cell line (RT112/84), thyroid cancer cell line (TT), cervical cancer cell line (Hela), leukemia cell line (K562), etc.), and then the plates were placed in a cell culture incubator.

2. On the second day of compound spiking experiment, prepare compounds, 10 concentration points of each compound to be tested and positive reference drug, dilute in culture medium with a 1:3 concentration gradient, and replicate the wells. Add 5 ul of compound to be tested or positive reference drug to the cell plate, the final concentration of compound to be tested is up to 10 uM, the final concentration of positive reference drug is up to 3 uM, and the concentration of DMSO is controlled below 0.2%, then place the cell plate in the cell incubator and incubate for 72 hours.

3. On the fifth day, 72 hours after treatment, CTG reagent (Promega G7573) was prepared according to the reagent instructions, and the configured CTG reagent and the cell plates were simultaneously placed at room temperature for 30 minutes for thermal equilibration. Then 50 ul of CTG reagent was added to each well of the cell plate, and the plate was mixed by low-speed shaking and placed at room temperature for 20 minutes and stored away from light. The cell culture plate was then placed on a plate reader (Envision or Viewlux) to record the data and analyze it to calculate the proliferation inhibition rate. The compound concentration corresponding to the 50% inhibition rate in the curve is the $IC_{50}$ for the proliferation inhibition of this compound on the tumor cell line.

Experiments for the Evaluation of Eleven Kinases Inhibitory Activities ($IC_{50}$)

In this experiment, the inhibitory effects of small molecule inhibitors on 17 kinases were examined by using fluorescent microfluidic mobility shift assay (Mobility-Shift Assay).

1. Buffer configuration: 50 mM HEPES, pH 7.5, 0.00015% Brij-35.
2. Compounds were configured in 100% DMSO in a concentration gradient and diluted with buffer to 10% DMSO, and added to 384-well plates. Compounds starting at 500 nM are prepared in 100% DMSO to 25 μM and diluted in a gradient of 10 concentrations, then diluted 10-fold in buffer to make an intermediate dilution of the compound containing 10% DMSO and transferred 5 μl to a 384-well plate.
3. The kinase was diluted to optimal concentration with the following buffers: 50 mM HEPES, pH 7.5, 0.00015% Brij-35, 2 mM DTT (final concentration of enzyme reaction: VEGFR-1 (FLT1): 2 nM; VEGFR-2 (KDR): 1.2 nM; VEGFR-3 (FLT4): 1.5 nM; FGFR1: 2 nM); FGFR2: 9 nM; FGFR3: 8 nM; FGFR4: 10 nM; PDGFRα: 3.5 nM; c-MET: 10 nM; RET: 7 nM; EGFR: 6 nM). Transfer 10 μl into a 384-well plate and incubate with the compounds for 10 min.
4. The substrate was diluted to the optimum concentration with the following buffer: 50 mM HEPES, pH 7.5, 0.00015% Brij-35. where the final concentration of the reaction was as follows:

VEGFR1 (FLT1): 3 μM Peptide30 (5-FAM-KKKKEE-IYFFF-CONH2), 278 μM ATP, 10 mM $MgCl_2$;

VEGFR2 (KDR): 3 μM Peptide22(5-FAM-EEPLYWSFPAKKK-CONH2), 92 μM ATP, 10 mM $MgCl_2$;

VEGFR3 (FLT4): 3 μM Peptide30 (5-FAM-KKKKEE-IYFFF-CONH2), 84 μM ATP, 10 mM $MgCl_2$;

FGFR1: 3 μM Peptide22(5-FAM-EEPLYWSFPAKKK-CONH2), 250 μM ATP, 10 mM $MgCl_2$;

FGFR2: 3 μM Peptide22(5-FAM-EEPLYWSFPAKKK-CONH2), 1.9 μM ATP, 10 mM $MgCl_2$;

FGFR3: 3 μM Peptide22(5-FAM-EEPLYWSFPAKKK-CONH2), 4.7 μM ATP, 10 mM $MgCl_2$;

FGFR4: 3 μM Peptide22(5-FAM-EEPLYWSFPAKKK-CONH2), 66 μM ATP, 10 mM $MgCl_2$;

PDGFRα: 3 μM Peptide22(5-FAM-EEPLYWSFPAKKK-CONH2), 134 μM ATP, 10 mM $MgCl_2$;

RET: 3 μM Peptide22(5-FAM-EEPLYWSFPAKKK-CONH2), 23 μM ATP, 10 mM $MgCl_2$ C-MET: 3 μM Peptide22(5-FAM-EEPLYWSFPAKKK-CONH2), 26 μM ATP, 10 mM $MgCl_2$;

EGFR: 3 μM Peptide22 (5-FAM-EEPLYWSFPAKKK-CONH2), 1 μM ATP, 10 mM MgCl2 were added into 384-well plate for 10 μl each and the reaction was started at 28° C. for 1 hour.

5. Read the conversion rate with Caliper Reader and calculate the conversion rate as suppression, formula Percent inhIcition=(max−conversion)/(max−min)*100.

6. Calculate the $IC_{50}$ formula Y=Bottom+(Top−Bottom)/(1+$(IC_{50}/X)$^HillSlope) by fitting it with XL-fit 5.4.0.8 software.

The hERG (potassium channel) is an important parameter in the safety of compounds involved in new drug studies. hERG mutations are highly expressed in the heart and are a major component of the rapid repolarization current (IKr) in the third phase of the myocardial action potential. hERG mutations cause a loss of function that is often associated with some inherited long QT syndromes (LQTS) and increase the risk of severe ventricular arrhythmias and torsional tachycardia is increased. The side effects caused by inhibition of potassium (K+) channels are one of the main reasons for the failure and scattering of new drug studies in recent years, and a compound with an in vitro inhibitory effect of hERG with an $IC_{50}$<30 uM may have the above mentioned pitfalls and risks. Therefore, in vitro inhibition of hERG channels ($IC_{50}$) evaluation has been recommended by the International Conference on Harmonization of Drug Registries as part of preclinical safety evaluation (ICHS7B Expert Working Group, '02).

Experimental Evaluation of the In Vitro Inhibitory Effect ($IC_{50}$) of hERG:

Stabilized cells were dropped onto circular slides and placed in a culture dish with a cell density below 50% and incubated overnight. Cells for experiments are transferred to a bath of approximately 1 ml embedded in an inverted microscope stage and perfused with extracellular fluid at a rate of 2.7 ml/min. The experiment can be started after 5 minutes of stabilization. Membrane currents were recorded using a HEKA EPC-10 membrane clamp amplifier and a PATCHMASTER acquisition system (HEKA Instruments Inc., D-67466 Lambrecht, Pfalz, Germany). All experiments were performed at room temperature (22~24° C.). A P-97 microelectrode puller (Sutter Instrument Company, One Digital Drive, Novato, CA 94949) was used to straighten the electrodes (BF150-110-10) in the experiments. The electrode had an inner diameter of 1-1.5 mm and an inlet resistance of 2-4 MΩ when filled with internal fluid. hERG potassium channels were electrophysiologically stimulated by first clamping the membrane voltage at −80 mV, giving the cells a continuous 2 s, +20 mV voltage stimulation to activate the hERG potassium channels, and then repolarizing to −50 mV for 5 s to generate an outward tail current with a stimulation frequency of every 15 s. Current values are the peak tail currents.

Channel currents were recorded in whole-cell recording mode in the experiments. First, the extracellular fluid (approximately 2 mL per minute) was perfused and recorded continuously, and the current was stabilized (Run-Down less than 5% for 5 minutes), at which point the peak tail current was the control current value. Next, the extracellular fluid containing the drug to be tested was instilled and recorded continuously until the inhibitory effect of the drug on the hERG current reached a steady state, at which point the peak tail current was the post-drug current value. The criterion for steady state was determined by the coincidence of the three most recent consecutive current recording lines. After reaching steady state, if the hERG current returned to or approached the size before the drug was added after washout with extracellular fluid, the test could be continued with other concentrations or drugs. 30 μM Quinidine (Quinidine) was used as a positive control in the experiment to ensure that the cells used responded normally.

TABLE 6

Results of hERG inhibition effect assay for three compounds

| | Compound Structure | hERG ($IC_{50}$, uM) |
|---|---|---|
| 1 | III-01 | >30 |
| 2 | Ref-1 (Lenvatinib) | 11.9 |
| 3 | Ref-2 | 15.4 |

Some of the preferred compounds such as Formula III (e.g., III-01) were tested for inhibition of various tumor cell lines (e.g., RT-112/84 and TT) and tyrosine kinases (e.g., KDR, FGFR4, EGFR, etc.) as shown in Tables 7, 8, 9, and 10 below; among them, the results showed that the inhibitory activity (IC50) of compound "III-18" was significantly better than that of control compounds such as "lenvatinib (Ref-1).

TABLE 7

Results of two cell lines and RTK target kinase inhibitory activity of some preferred formula III compounds

| | Samples | RT112/84 (uM) | TT (uM) | KDR (nM) | FGFR4 (nM) | EGFR (nM) |
|---|---|---|---|---|---|---|
| 1 | III-01 | 0.13 | 1.5 | 0.6 | 17 | 58 |
| 2 | Ref-1 | 0.29 | >10 | 5.1 | 65 | >1000 |
| 3 | Ref-2 | 0.42 | 6.4 | 8.6 | 39 | >1000 |

The range of activity ($IC_{50}$) of each compound in inhibiting hepatocellular carcinoma cell line (Hep3B 2.1-7) is labeled as "A" for <2.5 uM, "B" for 2.5-5.0 uM, and "C" for >5.0 uM. are labeled as "C";

The range of activity ($IC_{50}$) of each compound in inhibiting bladder tumor cell line (RT-112/84) is labeled as "A" for <0.2 uM, "B" for 0.2-1.0 uM, and "C" for >1.0 uM is labeled as "C";

The range of activity ($IC_{50}$) of each compound to inhibit thyroid tumor cell lines (TT) is labeled "A" for <5 uM, "B" for 5-10 uM, and "C" for >10 uM;

The activity effect range ($IC_{50}$) of each compound to inhibit hepatocellular carcinoma cell line (Hela) is labeled as "A" for <5.0 uM, "B" for activity range 5.0-10 uM, and "C" for activity range >10 uM. "C";

The activity effect range ($IC_{50}$) of each compound to inhibit leukemia cell line (K562) is labeled as "A" for <5.0 uM, "B" for activity range of 5.0-10 uM, and "C" for activity range >10 uM. "C".

TABLE 8

Inhibition activity results of liver cancer, bladder cancer, cervical cancer, thyroid tumor, and leukemia with some preferred formula III compounds

| | Samples | Hep3B 2.1-7 | RT112/84 | TT | Hela | K562 |
|---|---|---|---|---|---|---|
| 1 | III-01 | A | A | A | B | B |
| 2 | III-02 | C | C | C | C | C |
| 3 | III-03 | C | C | C | C | C |
| 4 | III-04 | C | C | C | C | C |
| 5 | III-05 | C | C | C | C | C |
| 6 | III-06 | C | C | C | C | C |
| 7 | III-07 | C | C | C | C | C |
| 8 | III-08 | C | C | C | C | C |
| 9 | III-09 | C | C | C | C | C |
| 10 | III-10 | C | C | C | C | C |
| 11 | III-11 | C | C | C | C | C |
| 12 | III-12 | C | C | C | C | C |
| 13 | III-13 | C | C | C | C | C |
| 14 | III-14 | C | C | C | C | C |
| 15 | III-15 | C | C | C | C | C |
| 16 | III-16 | B | B | C | C | B |
| 17 | III-17 | C | C | C | C | C |
| 18 | III-18 | C | C | C | C | C |
| 19 | III-19 | C | C | C | C | C |
| 20 | III-20 | C | C | C | C | C |
| 21 | III-21 | C | C | C | C | C |
| 22 | III-22 | C | C | C | C | C |
| 23 | III-23 | C | C | C | C | C |
| 24 | III-24 | C | C | C | C | C |
| 25 | III-25 | C | C | C | C | C |
| 26 | III-26 | C | C | C | C | C |
| 27 | III-27 | C | C | C | C | C |
| 28 | III-28 | C | C | C | C | C |
| 29 | III-29 | C | C | C | C | C |
| 30 | III-30 | C | C | C | C | C |

TABLE 8-continued

Inhibition activity results of liver cancer, bladder cancer, cervical cancer, thyroid tumor, and leukemia with some preferred formula III compounds

|    | Samples    | Hep3B 2.1-7 | RT112/84 | TT | Hela | K562 |
|----|------------|-------------|----------|----|------|------|
| 31 | III-31     | C | C | C | C | C |
| 32 | III-32     | C | C | C | C | C |
| 33 | III-33     | C | C | C | C | C |
| 34 | III-34     | C | C | C | C | C |
| 35 | III-35     | C | C | C | C | C |
| 36 | III-36     | C | C | C | C | C |
| 37 | III-37     | C | C | C | C | C |
| 38 | III-38     | C | C | C | C | C |
| 39 | III-39     | C | C | C | C | C |
| 40 | III-40     | C | C | C | C | C |
| 41 | III-41     | C | C | C | C | C |
| 42 | III-42     | C | C | C | C | C |
| 43 | III-43     | C | C | C | C | C |
| 44 | III-44     | C | C | C | C | C |
| 45 | III-45     | C | C | C | C | C |
| 46 | III-46     | C | C | C | C | C |
| 47 | III-47     | C | C | C | C | C |
| 48 | III-48     | C | C | C | C | C |
| 49 | III-49     | C | C | C | C | C |
| 50 | III-50     | C | C | C | C | C |
| 51 | III-51     | C | C | C | C | C |
| 52 | III-52     | C | C | C | C | C |
| 53 | Lenvatinib | C | B | C | C | B |
| 54 | Sorafenib  | C | C | C | C | C |
| 55 | Regorafenib| C | B | C | C | C |

The results of the activity of the preferred compounds of Formula III, respectively, for inhibition of RTK targets such as VEGFR1-3, FGFR1-4, c-MET, and RET, are presented in Table 9 below; wherein, the activity effect range ($IC_{50}$) of each compound for inhibition of various tyrosine kinases VEGFR2 (KDR) at <2.0 nM is labeled as "A", the activity range of 2.0-10 nM is labeled as "B", and the activity range >10 nM is labeled as "C"; The range of activity effects ($IC_{50}$) of each compound to inhibit various tyrosine kinases FGFR1-4 is labeled as "A" for <30 nM, "B" for 30-100 nM, and "C" for >100 nM. "C"; The range of activity ($IC_{50}$) of each compound to inhibit various tyrosine kinases EGFR is labeled "A" for <60 nM, "B" for 60-100 nM, and "C" for >100 nM; The range of activity ($IC_{50}$) of each compound to inhibit various tyrosine kinases C-MET is labeled "A" for <60 nM, "B" for 60-100 nM, and "C" for >100 nM.

TABLE 9

Inhibition activity results of five tyrosine kinases with some preferred formula III compounds

|    | Samples | KDR | FGFR2 | FGFR4 | EGFR | C-MET |
|----|---------|-----|-------|-------|------|-------|
| 1  | III-01  | A | A | A | A | B |
| 2  | III-02  | C | C | C | C | C |
| 3  | III-03  | C | C | C | C | C |
| 4  | III-04  | C | C | C | C | C |
| 5  | III-05  | C | C | C | C | C |
| 6  | III-06  | C | C | C | C | C |
| 7  | III-07  | C | C | C | C | C |
| 8  | III-08  | C | C | C | C | C |
| 9  | III-09  | C | C | C | C | C |
| 10 | III-10  | C | C | C | C | C |
| 11 | III-11  | C | C | C | C | C |
| 12 | III-12  | C | C | C | C | C |
| 13 | III-13  | C | C | C | C | C |
| 14 | III-14  | C | C | C | C | C |
| 15 | III-15  | C | C | C | C | C |
| 16 | III-16  | B | B | C | C | B |
| 17 | III-17  | C | C | C | C | C |
| 18 | III-18  | C | C | C | C | C |
| 19 | III-19  | C | C | C | C | C |
| 20 | III-20  | C | C | C | C | C |
| 21 | III-21  | C | C | C | C | C |
| 22 | III-22  | C | C | C | C | C |
| 23 | III-23  | C | C | C | C | C |
| 24 | III-24  | C | C | C | C | C |
| 25 | III-25  | C | C | C | C | C |
| 26 | III-26  | C | C | C | C | C |
| 27 | III-27  | C | C | C | C | C |
| 28 | III-28  | C | C | C | C | C |
| 29 | III-29  | C | C | C | C | C |
| 30 | III-30  | C | C | C | C | C |
| 31 | III-31  | C | C | C | C | C |
| 32 | III-32  | C | C | C | C | C |
| 33 | III-33  | C | C | C | C | C |
| 34 | III-34  | C | C | C | C | C |
| 35 | III-35  | C | C | C | C | C |
| 36 | III-36  | C | C | C | C | C |
| 37 | III-37  | C | C | C | C | C |
| 38 | III-38  | C | C | C | C | C |
| 39 | III-39  | C | C | C | C | C |
| 40 | III-40  | C | C | C | C | C |
| 41 | III-41  | C | C | C | C | C |
| 42 | III-42  | C | C | C | C | C |
| 43 | III-43  | C | C | C | C | C |
| 44 | III-44  | C | C | C | C | C |
| 45 | III-45  | C | C | C | C | C |
| 46 | III-46  | C | C | C | C | C |
| 47 | III-47  | C | C | C | C | C |
| 48 | III-48  | C | C | C | C | C |
| 49 | III-49  | C | C | C | C | C |
| 50 | III-50  | C | C | C | C | C |
| 51 | III-51  | C | C | C | C | C |
| 52 | III-52  | C | C | C | C | C |
| 53 | Lenvatinib | B | B | B | C | C |
| 54 | Sorafenib  | C | C | C | C | C |
| 55 | Regorafenib| C | B | C | C | C |

TABLE 10

Inhibition activity results of twelve tyrosine kinases with the formula III compound III-01 and two drug References

|    | Kinase name | III-01 ($IC_{50}$, nM) | Lenvatinib ($IC_{50}$, nM) | Regorafenib ($IC_{50}$, nM) |
|----|-------------|------------------------|----------------------------|------------------------------|
| 1  | VEGFR-1  | 3.7  | 13    | 55    |
| 2  | VEGFR-2  | 0.6  | 5.1   | 16    |
| 3  | VEGFR-3  | 1.1  | 3.2   | 34    |
| 4  | FGFR-1   | 14   | 56    | 158   |
| 5  | FGFR-2   | 11   | 27    | 43    |
| 6  | FGFR-3   | 22   | 59    | 62    |
| 7  | FGFR-4   | 17   | 65    | >500  |
| 8  | RET      | 2.5  | 6.4   | 12    |
| 9  | PDGFRα   | 7.9  | 27    | 16    |
| 10 | EGFR     | 53   | >1000 | >1000 |
| 11 | C-MET    | 96   | >1000 | >1000 |
| 12 | ABL      | 68   | >500  | >500  |

From the test results in Tables 7, 8, 9 and 10 above, it can be found that the compound "III-18" listed in the above tables has a better inhibitory effect on various tumor cell lines and tyrosine kinases, and its inhibitory activity and safety parameters such as hERG are significantly better than those of the already marketed control drugs such as Lenvatinib and Regorafenib.

Example 56: Toxicity Screening Test for Compound III-01

In order to test the toxicity of the new compound "III-01", which is the more active and preferred compound in Tables 6-7 above, MTD (60 mg/kg) and 14-day safety toxicity tests were conducted in rats. The MTD (300 mg/kg, QD) was administered to rats without any abnormalities such as death. The 28-day GLP toxicity test also used healthy rats at three doses (50 mg/kg, 100 mg/kg, 150 mg/kg), and the three groups of rats were administered once a day by gavage, and the toxicity of the test substance was evaluated by observing the toxicity response of the experimental animals for 28 consecutive days. The autopsy results of the three groups of rats and dogs also did not reveal any abnormal changes in various organs such as heart, liver, lung, kidney, stomach and intestine in vivo, and the compounds tested were generally found to be safe and non-toxic within the appropriate doses. Therefore, the preferred compound "III-01" designed and synthesized by the present invention not only has better inhibitory activity, but also has better safety and drug-forming properties, which is worthy of further clinical trials and application.

In summary, The compound "III-01", which was discovered in the multi-targeted antitumor innovation drug study, not only has better inhibitory activity, but also has better safety in the 28-day GLP toxicity test (50 mg/kg, 100 mg/kg, 150 mg/kg) in three groups of rats (better than the three publicly reported doses of the control drug "lenvatinib": 3 mg/kg, 10 mg/kg, 30 mg/kg). The results of hERG (>30 uM) and Ames assay (negative) showed no relevant side effects, and the relevant inhibitory activity and safety results were much better than those of the known control compounds such as lenvatinib and Regorafenib.

Finally, the present invention has discovered and provided a highly effective and safe antitumor RTK inhibitor III-01 for clinical trials in Q4, 2022. So far, all preclinical studies of the compound III-01 have been finished with excellent results as expected, and its IND application for clinical trials has been submitted to CDE in China and FDA in USA in July, 2022.

What is claimed is:

1. A compound represented by formula III, or a stereoisomer, tautomer, deuterate, pharmacologically acceptable salt, or hydrate thereof:

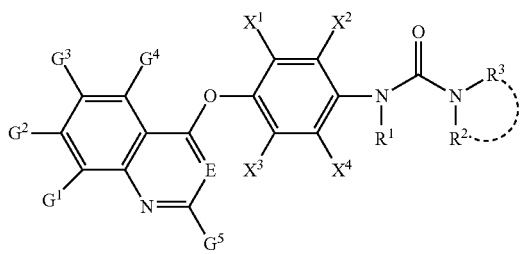

III wherein:
- E is independently selected from the group consisting of nitrogen (N), or CH group;
- $G^1$ is independently selected from H, deuterium (D), $C_{1-20}$ alkyl group, or $C_{1-20}$ alkoxy group;
- $G^2$ is independently selected from $C_{1-20}$ alkoxy, or optionally deuterium-substituted $C_{1-20}$ alkoxy group;
- $G^3$ is independently selected from —C(O)NH$_2$, —C(O)ND$_2$, or an optionally substituted $C_{1-20}$ alkoxy group;
- $G^4$ and $G^5$ are each, independently, selected from hydrogen (H), deuterium (D), halogen, —CN, $C_{1-20}$ alkyl, or $C_{1-20}$ alkoxy group;
- $R^1$ is independently selected from hydrogen (H), deuterium (D), $C_{1-20}$ alkyl, $C_{3-20}$ cycloalkyl, or —$C_{3-20}$ deuterated cycloalkyl group;
- $R^2$ and $R^3$ are each, independently, selected from hydrogen (H), deuterium (D), $C_{1-20}$ alkyl, $C_{3-20}$ cycloalkyl, $C_{3-20}$ deuterated cycloalkyl group, or $C_{3-20}$ heterocycloalkyl group; wherein $R^2$ and $R^3$ may be linked to each other to form $C_{3-20}$ heterocyclic group with 1-3 heteroatoms;
- $X^1$, $X^2$ and $X^3$ are each, independently, selected from halogen, —CN, —NH$_2$, $C_{1-20}$ alkoxy group, or $C_{1-20}$ alkyl amino group;
- $X^4$ is independently selected from H, deuterium (D), halogen, —NH$_2$, $C_{1-20}$ alkoxy, or $C_{1-20}$ alkyl amino group.

2. The compound according to claim 1, wherein
- E is independently selected from nitrogen (N) or CH group;
- $G^1$ is independently selected from H, deuterium (D), $C_{1-12}$ alkyl group, or $C_{1-12}$ alkoxy group;
- $G^2$ is independently selected from $C_{1-12}$ alkoxy, or optionally deuterium-substituted $C_{1-12}$ alkoxy group;
- $G^3$ is independently selected from —C(O)NH$_2$, —C(O)ND$_2$, or an optionally substituted $C_{1-12}$ alkoxy group;
- $G^4$ and $G^5$ are each, independently, selected from hydrogen (H), deuterium (D), halogen, CN, $C_{1-12}$ alkyl, or $C_{1-12}$ alkoxy group;
- $R^1$ is independently selected from hydrogen (H), deuterium (D), $C_{1-12}$ alkyl, $C_{3-12}$ cycloalkyl, or —$C_{3-12}$ deuterated cycloalkyl group;
- $R^2$ and $R^3$ are each, independently, selected from hydrogen (H), deuterium (D), $C_{1-12}$ alkyl, $C_{3-12}$ cycloalkyl, $C_{3-12}$ deuterated cycloalkyl group, or $C_{3-12}$ heterocycloalkyl group; wherein $R^2$ and $R^3$ may be linked to each other to form $C_{3-12}$ heterocyclic group with 1-3 heteroatoms;
- $X^1$, $X^2$ and $X^3$ are each, independently, selected from hydrogen (H), deuterium (D), halogen, —CN, —NH$_2$, $C_{1-12}$ alkoxy group, or $C_{1-12}$ alkyl amino group;
- $X^4$ is independently selected from H, deuterium (D), halogen, —NH$_2$, $C_{1-12}$ alkoxy, or $C_{1-12}$ alkyl amino group.

3. The compound according to claim 2, wherein
- E is independently selected from nitrogen (N) or CH group;
- $G^1$ is independently selected from H, deuterium (D), $C_{1-6}$ alkyl group, or $C_{1-6}$ alkoxy group;
- $G^2$ is independently selected from $C_{1-6}$ alkoxy or optionally deuterium-substituted $C_{1-6}$ alkoxy group;
- $G^3$ is independently selected from —C(O)NH$_2$, —C(O)ND$_2$, or an optionally substituted $C_{1-6}$ alkoxy group;
- $G^4$ and $G_5$ are each, independently, selected from hydrogen (H), deuterium (D), halogen, CN, $C_{1-6}$ alkyl, or $C_{1-6}$ alkoxy group;

R¹ is independently selected from hydrogen (H), deuterium (D), $C_{1-6}$ alkyl, $C_{3-6}$ cycloalkyl, or $C_{3-6}$ deuterated cycloalkyl group;

R² and R³ are each, independently, selected from hydrogen (H), deuterium (D), $C_{1-6}$ alkyl, $C_{3-6}$ cycloalkyl, $C_{3-6}$ deuterated cycloalkyl group, or $C_{3-6}$ heterocycloalkyl group; wherein R² and R³ may be linked to each other to form $C_{3-6}$ heterocyclic group with 1-3 heteroatoms;

X¹, X² and X³ are each, independently, selected from hydrogen (H), deuterium (D), halogen, —CN, —NH₂, $C_{1-6}$ alkoxy group, or $C_{1-6}$ alkyl amino group;

X⁴ is independently selected from H, deuterium (D), halogen, —NH₂, $C_{1-6}$ alkoxy, or $C_{1-6}$ alkyl amino group.

4. The compound according to claim 3, wherein

E is CH group,

G¹ is hydrogen (H);

G² is —OCH₃;

G³ is —C(O)NH₂;

G⁴ is hydrogen (H);

G⁵ is hydrogen (H);

R¹ is hydrogen (H);

R² is hydrogen (H);

R³ is each independently selected from $C_{3-6}$ cycloalkyl group;

X¹, X² and X³ are each, independently, selected from halogen, $C_{1-6}$ alkoxy group, or $C_{1-6}$ alkyl amino group;

X⁴ is independently selected from hydrogen (H), halogen, $C_{1-6}$ alkoxy group, or $C_{1-6}$ alkyl amino group.

5. The compound according to claim 4, which is represented by the following structure:

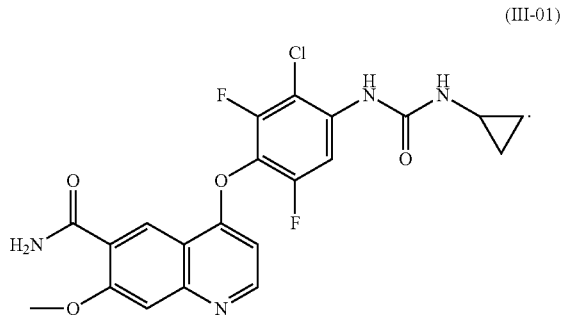 [SMILES: COc1cc2nccc(Oc3c(F)cc(NC(=O)NC4CC4)c(Cl)c3F)c2cc1C(N)=O]

(III-01)

6. A pharmaceutical composition comprising the compound according to claim 1.

7. A composition comprising at least one compound according to claim 1 and at least one compound selected from the group consisting of a tyrosine kinase (RTK) inhibitor.

8. A method of treating cancer, comprising administering an effective amount of the compound according to claim 1 to a subject in need thereof.

9. A method according to claim 8, wherein the treated cancer is selected from the group consisting of liver cancer, bladder cancer, thyroid cancer, cervical cancer, and blood cancer.

10. A composition comprising at least one compound according to claim 1 and at least one compound selected from (1) an immunomodulator, (2) PD-1 inhibitor, (3) PD-L1 inhibitor, or (4) another active ingredient that does not fall under (1)-(3) above.

* * * * *